United States Patent [19]

Christensen et al.

[11] 4,150,223
[45] Apr. 17, 1979

[54] CEPHALOSPORIN PHOSPHONIC ACID, SULFONIC ACID AND SULFONAMIDE COMPOUNDS

[75] Inventors: Burton G. Christensen, Scotch Plains; Ronald W. Ratcliffe, North Plainfield, both of N.J.

[73] Assignee: Merck & Co., Inc., Rahway, N.J.

[21] Appl. No.: 901,159

[22] Filed: Apr. 28, 1978

Related U.S. Application Data

[60] Continuation of Ser. No. 768,796, Feb. 15, 1977, abandoned, which is a division of Ser. No. 410,831, Nov. 8, 1973, Pat. No. 4,032,521, which is a continuation-in-part of Ser. No. 319,946, Dec. 29, 1972, abandoned.

[51] Int. Cl.$^2$ .................................. C07D 501/18
[52] U.S. Cl. .................................. 544/16; 544/21; 544/24; 544/26; 544/29; 544/30; 544/22; 424/200; 424/246
[58] Field of Search .................. 544/21, 24, 26, 28, 544/29, 30, 27, 16; 424/246

[56] References Cited

U.S. PATENT DOCUMENTS

| | | | |
|---|---|---|---|
| 3,801,567 | 4/1974 | Heusler et al. | 260/239.1 |
| 3,856,785 | 12/1974 | Breuer et al. | 544/28 |
| 3,966,719 | 6/1976 | Barth | 544/23 |
| 4,014,872 | 3/1977 | Cocker | 544/16 |

FOREIGN PATENT DOCUMENTS 2337446  2/1975  Fed. Rep. of Germany ............ 544/30

Primary Examiner—Donald G. Daus
Assistant Examiner—Diana G. Rivers
Attorney, Agent, or Firm—Frank M. Mahon; James A. Arno; Julian S. Levitt

[57] ABSTRACT

Novel antibiotics of the formula:

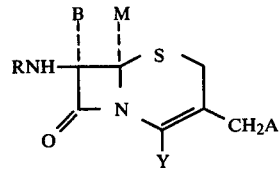

and its salts, esters and amides wherein R is acyl; B is H, $OCH_3$, $CH_3$ or $SR''$ wherein $R''$ is lower alkyl; A is hydrogen, hydroxy, or an organic group; and, Y is a radical of the formula $PO(OH)_2$; $PO(OH)(OR'')$ wherein $R''$ is loweralkyl; $SO_2(OH)$; or $SO_2NH_2$.

The products are prepared by a multi-step process starting with an α-aminophosphonoacetate and terminating in the acylation of the 7-amino compound, and, if desired, removing the ester blocking group. The products are useful antibiotics.

1 Claim, No Drawings

CEPHALOSPORIN PHOSPHONIC ACID, SULFONIC ACID AND SULFONAMIDE COMPOUNDS

BACKGROUND OF THE INVENTION

This application is a continuation of U.S. Application Ser. No. 768,796, filed Feb. 15, 1977, now abandoned, which is a division of U.S. Application Ser. No. 410,831, filed Nov. 8, 1973, now U.S. Pat. No. 4,032,521, issued June 28, 1977, which in turn is a continuation-in-part of U.S. Application Ser. No. 319,946, filed Dec. 29, 1972, now abandoned.

This invention is directed to novel antibiotics, novel intermediates and processes for preparing them. The novel antibiotics are effective against gram-negative bacteria including *Proteus vulgaris, E. coli,* and *Salmonella schottmulleri,* and gram-positive bacteria including *Staphylococcus aureus* and *Bacillus subtilis.*

The products are useful in removing susceptible microorganisms from pharmaceutical, medical and dental equipment and as bactericides in industrial applications, for example, in water based paints and in the white water of paper mills to inhibit the growth of harmful bacteria.

The novel compounds of this invention have the following structural formula:

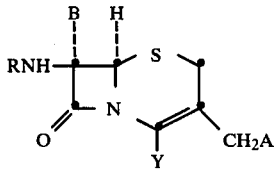

wherein B is H, $OCH_3$, $CH_3$, $SR''$, wherein $R''$ is loweralkyl of 1-6 carbon atoms (e.g., methyl, ethyl, propyl, butyl, hexyl); R is an acyl radical, for example, an aliphatic, aromatic, heterocyclic araliphatic or heterocyclic aliphatic carboxylic acid radical of the formula:

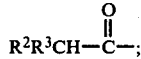

A is hydrogen, hydroxy, carbamoyloxy, thiocarbamoyloxy, quaternary ammonium, N-lower alkyl carbamoyloxy such as N-methyl carbamoyloxy and the like, N,N-di-lower alkyl carbamoyloxy such as N,N-dimethyl carbamoyloxy and the like, N-loweralkylthio and N,N-diloweralkylthiocarbamoyloxy, azido, halo, cyano, a tertiary amine such as pyridinium, alkylpyridinium, halopyridinium, aminopyridinium and the like, acyloxy for example, lower alkanoyloxy such as acetoxy, propionyloxy and the like, or aroyloxy such as benzoyloxy and the like, or a 5-member heterocyclic thio group having 1-4 hetero atoms, the latter being S, O or N; and Y is $PO(OH)_2$; $PO(OH)(OR'')$ wherein $R''$ is loweralkyl of 1-6 carbon atoms; $SO_2(OH)$; or $SO_2NH_2$.

Also included within the scope of the above generic formula are non-toxic pharmacologically acceptable salts, amides and esters.

By the phrase a "(5-membered heterocyclic)thio group having 1-4 hetero atoms, the latter being S, O or N" is meant a group having the structure

—S—Q wherein Q is a 5-membered heterocyclic ring having oxa, aza, thia, dioxa, diaza, dithia, trioxa, triaza, trithia, tetra-aza, or mixed hetero atoms in the ring. Included within this definition are the heterocyclic rings listed above, as well as the following additional rings: 1H-tetrazole; 2H-tetrazole; 3H-1,2,3-oxathiazole; 1,4,2-oxathiazole; 5H-1,2,5-oxathiazole; 3H-1,2,4-dioxazole; 1,3,4-dioxazole; 1,2,4-dithiazole; 1,3,4-dithiazole; 1,2,3-oxadiazole; 1,2,4-oxadiazole; 1,2,5-oxadiazole; 1,3,4-oxadiazole; 1,2,3-thiadiazole; 1,2,4-thiadiazole; 1,2,5-thiadiazole; 1,3,4-thiadiazole; 1H-1,2,3-triazole; 1,2,5-oxadithiole; 1,3,2-dioxathiole; 1,2,3-trioxole; 1,2,4-trioxolane, 1,2,3-trithiole; 1,2,4-trithiolane, etc. The point of attachment can be in any suitable position of the ring.

Other suitable rings can be found in the literature, including the ACS monograph, *The Ring Index;* Ed. Capell et. al., Second Edition (1957) and supplements (1959), (1963), (1965).

Representative of the hetero groups of interest that may be employed in the practice of the invention include furyl, thienyl, thiazolyl, thiadiazolyl, pyrrolyl, pyrazolyl, tetrazolyl, and the like or a substituted heterocyclic group having one or more alkyl, alkoxy, halo, cyano or carboalkoxy and the like. Two heterocyclicthio groups of particular interest are 5-methyl-1,3,4-thiadiazolyl-2-yl and 1-methyl-tetrazol-5-yl.

Those compounds wherein the acyl radical, R, is of the formula:

wherein $R^2$ and $R^3$ are as defined below, and $A^1$ is hydrogen, lower alkanoyloxy, heterocyclicthio, carbamoyloxy, or pyridinium represent a preferred group of radicals because of the generally enhanced antibiotic activity of the compounds containing these radicals. $R^2$ represents hydrogen, halo, amino, guanidino, phosphono, hydroxy, tertrazolyl, carboxy, sulfo or sulfamino. $R^3$ represents phenyl, substituted phenyl, a 5- or 6-membered monocyclic heterocycle containing one or more oxygen, sulfur or nitrogen hetero atoms in the ring such as furyl, thienyl, thiazolyl, isothiazolyl, tetrazolyl, oxadiazolyl, thiadiazolyl and the like, substituted heterocycles, phenylthio, phenyloxy, heterocyclic or substituted heterocyclithio groups or cyano. The substituents can be halo, carboxymethyl, guanidino, guanidinomethyl, carboxyamidomethyl, aminomethyl, nitro, methoxy or methyl. Especially preferred are those acyl radicals where $R^2$ is hydrogen, hydroxy, amino, carboxy and $R^3$ is phenyl or a 5- or 6-membered heterocyclic ring containing from 1 to 4 sulfur, oxygen or nitrogen atoms. Examples of these preferred radicals are phenylacetyl, 3-bromophenylacetyl, p-aminomethylphenylacetyl, 4-carboxymethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 2-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, 1-tetrazolylacetyl, α-fluorophenylacetyl, D- phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadieneacetyl, α-sulfaminophenylacetyl, α-hydroxyphenylacetyl, α-tetrazolylphenylacetyl and α-sulfophenylacetyl.

However, it is to be understood that any acyl radical that is conventionally employed in the cephalosporin and penicillin antibiotic art may be employed in the practice of the invention and is to be considered within the scope of the invention. Additional illustrations of representative acyl moieties are as follows:

The acyl radical can be a substituted or unsubstituted aliphatic, aromatic or heterocyclic, araliphatic or heterocylylaliphatic carboxylic acid radical or a carbothioic acid radical such as the acyl radicals of the known cephalosporins and penicillins. These acyl radicals can be represented by the general formula:

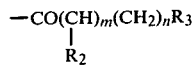

where $R_2$ is a radical of the group defined below, m and n represent 0–4 and $R_3$ represents R″ or ZR″, which are defined below.

One group of acyl radicals can be represented by the general formula

wherein $R^4$ represents a substituted or unsubstituted straight or branched chain alkyl, alkenyl, or alkynyl group; aryl, aralkyl; cycloalkyl; or a heteroaryl or heteroaralkyl group. These groups can be unsubstituted or can be substituted by radicals such as OH, SH, SR (R is alkyl or aryl), alkyl, alkoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein $R^4$ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-quanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl) methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl) methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

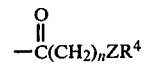

wherein n is 0–4, Z represents oxygen or sulfur, and $R^4$ is defined as above. Representative members of the substituent

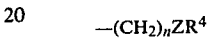

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxy)phenylthiomethyl, p-(carboxymethyl)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio.

Alternatively, the acyl group can be a radical of the formula

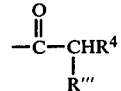

wherein $R^4$ is defined as above and R‴ is a radical such as amino, hydroxy, azido, carbamoyl, quanidino, acyloxy, halo, sulfamino, tetrazolyl, sulfo, carboxy, carbalkoxy, and the like.

Also of interest is the following acyl moiety:

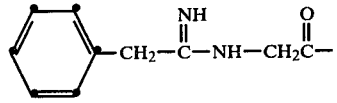

Representative members of the substituent

that might be mentioned are α-aminobenzyl, 2-thienylaminomethyl, α-methylaminobenzyl, α-amino-methylmercaptopropyl, α-amino-3- or 4-chlorobenzyl, α-amino-3 or 4-hydroxybenzyl, α-amino-2,4-dichlorobenzyl, α-amino-3,4-dichlorobenzyl, D-(—)-α-hydroxybenzyl, α-carboxybenzyl, 3-thienyl-aminomethyl D-(—)-α-amino-3-chloro-4-hydroxybenzyl, D(—)-3-thienylaminomethyl or 1-aminocyclohexyl, α-(5-tetrazolyl)-benzyl, 2-thienyl-carboxymethyl, 3-thienyl-carboxymethyl, 2-furyl-carboxymethyl, 3-furyl-carboxymethyl, α-sulfaminobenzyl, 3-thienyl-sulfaminomethyl, α-(N-methylsulfamino)benzyl, D(—)-2-thienyl-guanidinomethyl D(—)-α-guanidinobenzyl, α-guanylureidobenzyl, α-hydroxybenzyl, α-azidobenzyl, α-fluorobenzyl, 2-methoxy-1,3,4-oxadiazolylaminomethyl, 2-(5-methoxy-1,3,4-oxadiazolyl)-hydroxymethyl, 2-(5-methoxy-1,3,4-oxadiazolyl)-carboxymethyl, 2-(5-methoxy-1,3,4-thiadiazolyl)-aminomethyl, 2-(5-methoxy-1,3,4-thiadiazolyl)-hydroxymethyl, 2-(5-methoxy-1,3,4-thiadiazolyl)carboxymethyl, 2(5-chlorothienyl)-aminomethyl, 2-(5-chlorothienyl)-hydroxymethyl, 2-(5-chlorothienyl)-carboxymethyl, 3-(1,2thiazolyl)-aminomethyl, 3-(1,2-thiazolyl)hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfonbenzyl, α-phosphonobenzyl, α-diethylphosphonobenzyl, and α-monoethylphosphonobenzyl.

Alternatively, the group

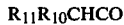

can be a sulfonamido group such as phenylsulfonamido, ethylsulfonamido, benzylsulfonamido, 2,5-dimethylbenzylsulfonamido, 4-chlorobenzylsulfonamido, 4-chlorophenylsulfonamido, 4-methoxybenzylsulfonamido, and the like.

The acyl substitutents of the general formula $R_{11}R_{10}CHCO$ wherein $R_{10}$ and $R_{11}$ are as defined below represent a preferred group of substitutents because of their generally useful antibiotic activity. $R_{10}$ represents hydrogen, halo, amino, guanidino, phosphono, hydroxy, tetrazolyl, carboxy, sulfo, or sulfamino. $R_{11}$ represents phenyl, substituted phenyl, a monocylcic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino.

Of particular interest are acyl represented by the formula:

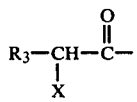

wherein X is hydrogen, halogen, amino, guanidino, phosphono, hydroxy, tetrazolyl, carboxy, sulfo, or sulfamino; $R_3$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1-6 carbon atoms), or cyano; the substituents on the $R_3$ group being halo, carboxymethy, guanidino, guanidinomethyl, carboxyamidomethyl, hydroxy, aminomethyl, nitro, methoxy or methyl. Particularly preferred are acyl groups where X is hydrogen, hydroxy, amino or carboxy and $R_3$ is phenyl, lower alkyl or a 5- or 6-membered heterocyclic ring having one or two sulfur, oxygen or nitrogen hetero atoms. Thus, specific $R_3$ substituents that might be mentioned as preferred substituents are tetrazolyl, thienyl, furyl and phenyl.

With respect to the term "A"; A can be a halo such as chloro, bromo or fluoro.

When A is substituted hydroxy or substituted mercapto group, it can be shown by the formula $-ZR_x$ where Z is oxygen or sulfur, and $R_x$ is an acyl group, a straight chain or branched chain loweralkyl (1-6 C), alkenyl (1-6 C) or alkynyl group (1-6 C); an aryl group; an aralkyl group; or a heterocyclic group such as heteroaryl or heteroalkyl. The heterocyclic group is preferably a 5- or 6-membered ring containing one or more sulfur, nitrogen or oxygen atoms. These groups can be unsubstituted or can be substituted by radicals such as alkyl (1-6 carbons), alkoxy (1-6 carbon atoms), halo, cyano, carboxy, carbamoyl, N-substituted carbamoyl, azido, sulfo, amino, substituted amino, haloalkyl, carboxyalkyl, carbamoylalkyl, N-substituted carbamoylalkyl, guanidino, N-substituted guanidino, guanidinoalkyl, sulfamyl, substituted sulfamyl, and the like.

Representative of the groups —x thus presented that might be mentioned are isoxazolylthio, pyrolidenylthio, 1,3,4-thiadiazolylthio, 1-oxidopyridylthio, furazanylthio, tetrazolylthio, thienylthio, thiazolylthio, furylthio, pyranylthio, pyrrolylthio, imidazolylthio, pyrazolylthio, pyridylthio, pyrazinylthio, pyrimidinylthio, pyridazinylthio, isothiazolylthio, methoxy, n-propoxy, methylthio, acetoxy, propionyloxy, benzoyloxy, (p-chlorobenzoyl)oxy, (p-methylbenzoyl)oxy, pivaloyloxy, (1-adamantyl)carboxy, butanoyloxy, carbamoyloxy, (N-methylcarbamoyl)oxy, (N-ethylcarbamoyl)-oxy, [N-(2-chloroethyl)carbamoyl]oxy, (N-phenylcarbamoyl)oxy, (N-p-sulfophenylcarbamoyl)oxy, p-carboxymethylphenylcarbamoyloxy, methoxycarbonyloxy, isobutanoyloxy, cyclobutylcarbonyloxy, carbamoylthio, (ethoxythiocarbonyl)thio, (N-lpropoxythiocarbonyl)thio, (cyclopentanoxythiocarbonyl)thio, methylthio, N,N-diethylthiocarbamoylthio, N-methylpiperazinium-1-thiocarbonylthio, N,N-dimethylpiperazinium-1-thiocarbonylthio, 2-furoylthio, isothiouronium, (5-methyl-1,3,4-thiadiazol-2-yl)thio, p-tolylsulfonylthio, mesyloxy, methyl-1,2,3,4-tetrazolyl-5-thio, tosyloxy, sulfamoyloxy, 1-naphthoyloxy, 2-furylacetoxy, cinnamoyloxy, p-hydroxycinnamoyloxy, p-sulfocinnamoyloxy and 1R:2S-epoxypropylphosphonyloxy.

The substituent A can also be a group of the general formula $-Y_1$ wherein $Y_1$ represents amino or substituted amino including nitrogen heterocycles and substituted heterocyclic groups. Examples of such groups that might be mentioned are amino, acetamido, carbamoylamino, N,N-dimethylamino, N-(2-chloroethyl)amino, 5-cyano-triazol-1-yl, 4-methoxycarbonyltriazol-1-yl.

Representative of the quaternary ammonium groups representing A that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarboxymethyl)pyridinium, 4-(hydroxymethyl)pyridinium, 4-(trifluoromethyl)pyridinium, quinolinium, picolinium and lutidinium.

The preferred groups representing A are hydrogen, halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5- or 5-membered hetero ring containing one or more nitrogen, oxygen or sulfur atoms. The acyl group can be a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted by radicals such as alkoxy, halo, amino, cyano, carboxy, sulfo and the like.

It may be noted that the substituent at the 3-position of the cephalosporin nucleus may be converted to or readily replaced by other A substituents pursuant to methods well known in this art. For example, upon treating the 3-acetoxymethyl substituted cephalosporanates of this invention with a suitable reagent or combination of reagents, it is possible to substitute various substituents for acetoxy at the 3-position of the cephalosporin nucleus. Suitable reagents include, for example, alkali metal toluenesulfinates, alkali metal azide, polyhydroxybenzene, N-loweralkyl indole, thiourea, mercaptans, heterocyclic thiols, cycloalkyl xanthates, pyridine; thiobenzoic acid, N-alkyl and N,N-dialkylthioureas or alkali metal N-alkyl and N,N-dialkylthiocarbamates and the like.

Thus by reaction with a heterocyclic thiol, for example, 1-methyl-1,2,3,4-tetrazole-5-thiol or 5-methyl-1,3-4-thiadiazole-2-thiol, the 3-acetoxymethyl-cephalosporin is converted to the corresponding heterothiomethyl compound.

Also, by reaction with a tertiary amine compound, for example, pyridine, the 3-acetoxymethylcephalosporin is converted to the corresponding 3-pyridiummethyl compound. Alternatively, the 3-acetoxymethylcephalosporins upon treatment with citrus acetylesterase are converted to the corresponding 3-hydroxymethyl compounds which can be acylated to produce other 3-acyloxymethyl including carbamoyloxymethyl. Similarly, other 3-substituted cephalosporin compounds are prepared following procedures well known in this art.

Thus, the acetoxy group of such compounds can be cleaved to produce the corresponding 3-hydroxymethyl compound by enzymatic hydrolysis with acetylesterase. The resulting hydroxy group may be then reacted to form other substituents at the 3-position. For example, the 3-hydroxy group may be re-esterified with a lower alkanoic acid group or with an aryl acid group by employing acylating agents such as a lower alkyl or aryl carboxylic acid halide or anhydride, a substituted carbamoyl halide, a lower alkyl isocyanate, or isothiocyanate or phosgene and a secondary amine.

The 3-acetoxy group may also be converted to other analogs by replacing the acetoxy group with nitrogen or sulfur nucleophiles. Many nitrogen and sulfur nucleophiles are well known in the cephalosporin art and the following examples are merely illustrative of the type of compound which may be employed; for example, a tertiary such as pyridine and the like, a 5-membered heterocyclic thiol such as 5-methyl-1,3,4-thiadiazolyl-2-thiol, N-methyltetrazolylthiol and the like. Alternatively, the 3-acetoxy group can be cleaved by catalytic hydrogenation to afford the 3-methyl compounds.

One method for the introduction of an N,N-diloweralkylcarbamoyloxymethyl or heterocyclic aminocarbonyloxyethyl moiety at position 3 of the instant products consists in treating a 3-hydroxymethyl analog such as a 3-hydroxymethyl-7-methoxy-7-(2-thienylacetamido)-ceph-3-em-4-phosphonic acid with phosgene and a diloweralkylamine in the presence of a base. In this manner the following products can be obtained: di-sodium dl-3-(N,N-dimethylcarbamoyloxymethyl)-7-methoxy-7-(2-thienylacetamido)-ceph-3-em-4-phosphonate and di-sodium dl-3-(pyrrolidinylcarbonyloxymethyl)-7-methoxy-7-(2-thienylacetamido)-ceph-3-em-4-phosphonate.

The N-mono sustituted carbamoyloxyethylcephalosporin products are obtained by treating a 3-hydroxymethyl-7-amido-3-cephem-4-phosphonate with a suitable isocyanate.

The unsubstituted carbamoyloxymethyl may be obtained by cleaving an N-mono- or di-substituted carbamoyloxymethyl material such as N,N-di-p-methoxybenzylcarbamoyloxymethyl or N-2,2,2-trichloroethyl carbamoyloxymethyl. An alternative method for obtaining the carbamoyloxymethyl group at the 3-position involves treating the 3-hydroxymethyl analog with trichloroacetylisocyanate or chlorosulfonylisocyanate, followed by hydrolysis.

The process for preparing the 7-acylamido compounds (I, supra) comprises treating the 7-amino or 7-substituted imino compound (II, infra) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, a mixed acid anhydride with other carboxylic acids and particularly lower alkyl esters of carboxylic acids; also, carboxylic acids in the presence of a carbodimide such as 1,3-dicyclohexylcarbodiimide, an activated ester of a carboxylic acid such as the p-nitrophenyl ester or by enzymatic acylation.

When an imino compound is employed increased yields are obtained when the imino compound is first treated with a metal catalyst. The first step comprises dissolving the imino compound in an inert solvent such as tetrahydrofuran, dimethylsulfoxide, dioxane, dimethylformamide, methanol, ethanol, methylene chloride or chloroform. A small amount of water is then added such that the solvent to water ratio is about 5-6:1. The metal catalyst is then added and the residue mixture stirred at ambient temperature for 1–5 hours. The solvent may be removed or the acylating agent added directly to the reaction mixture. The catalyst is of the formula $ML_n$ where M is a metal such as palladium, platinum, nickel, ruthenium, rhodium, cobalt or iron; L is the ligand such as halo; carbonyl; cyclopentadienyl; phenylcyano and the like and n is an integer which is equal to the valence requirements. Palladium chloride ($PdCl_2$) is the preferred catalyst.

The acylation reaction may be conducted at a temperature in the range of from about $-20°$ C. to about $100°$ C. but is preferably conducted at a temperature in the range of from $0°$ C., to $25°$ C. Any solvent in which the reactants are soluble and substantially inert may be employed, for example, hydrocarbons such as benzene, toluene, and the like or tertiary amines, for example, trialkylamines and heterocyclic amines such as trimethylamine, pyridine and the like, also methylene chloride, chloroform, ethylacetate or diethylether may be employed. The reaction is conducted for a period of time of from about five minutes to a maximum of three hours, but in general, a reaction time of about 0.5 to about one hour is sufficient. The following equation illustrates this process employing the carboxylic acid halide; however, it is to be understood that by substituting the corresponding carboxylic acid anhydride or other functionally equivalent acylating agents similar products may be obtained.

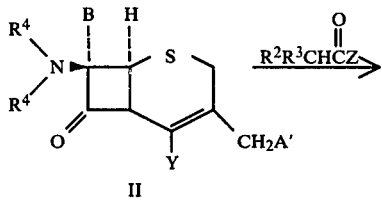

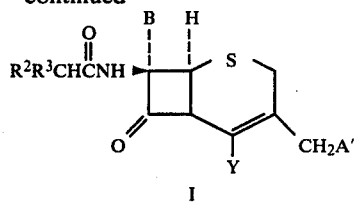

wherein $R^2$, $R^3$, and B are as defined above; $A^1$ is hydrogen, lower alkanoyloxy, heterocyclic thio, or carbamoyloxy; $R^4$ is hydrogen, or both $R^4$ groups taken together is benzylidene or substituted benzylidene, and Z is halo, for example, chloro, bromo and the like.

The 7β-amine and 7β-substituted imino compounds, (IIa and IIb, respectively, infra) ae prepared by various processes depending upon the nature of the 7α-substituent. When it is hydrogen, the procedure depicted in Flow Sheet I is employed. When the 7α-substituent is methoxy, the process of Flow Sheet II is employed; Flow Sheets III and IV, respectively, refer to 7α-methyl and 7α-alkylthio.

Flow Sheet I, 7α Hydrogen

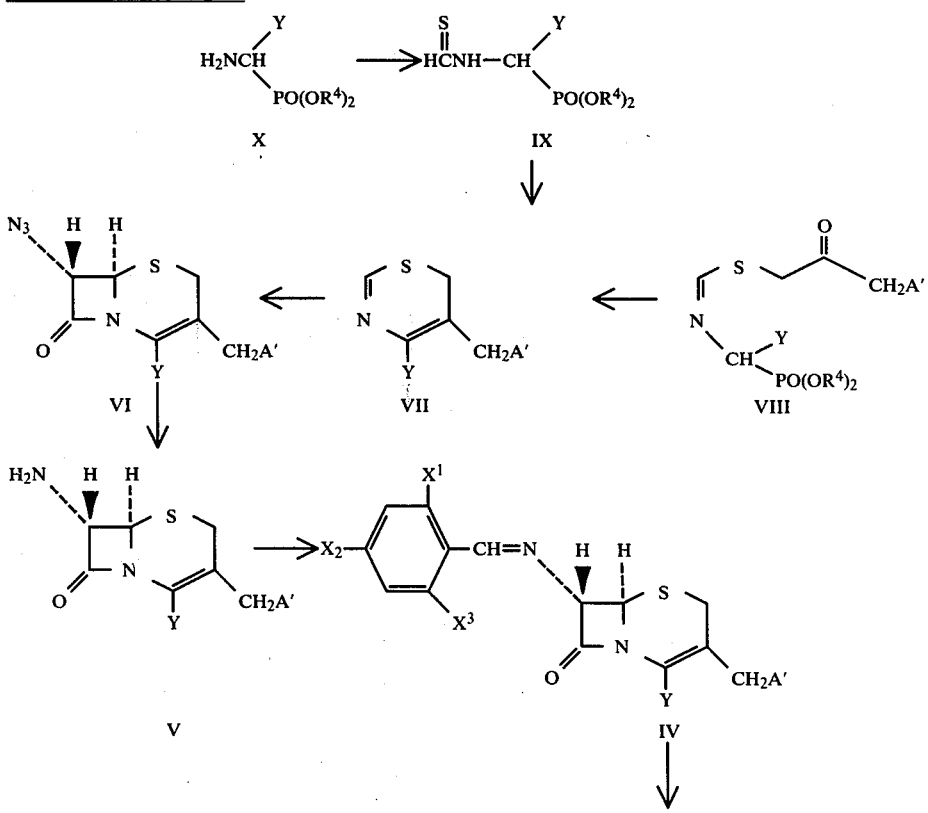

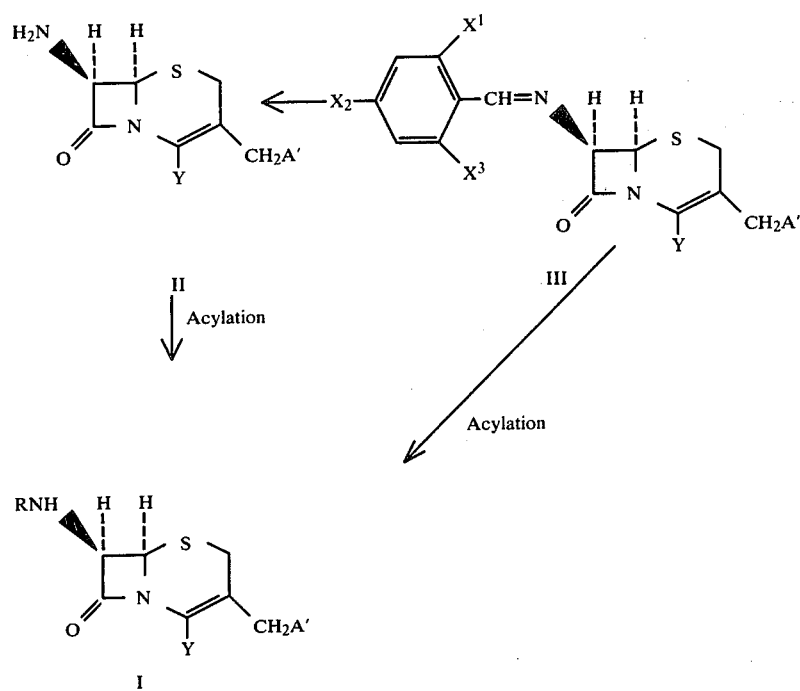
Flow Sheet II 7α-OCH₃
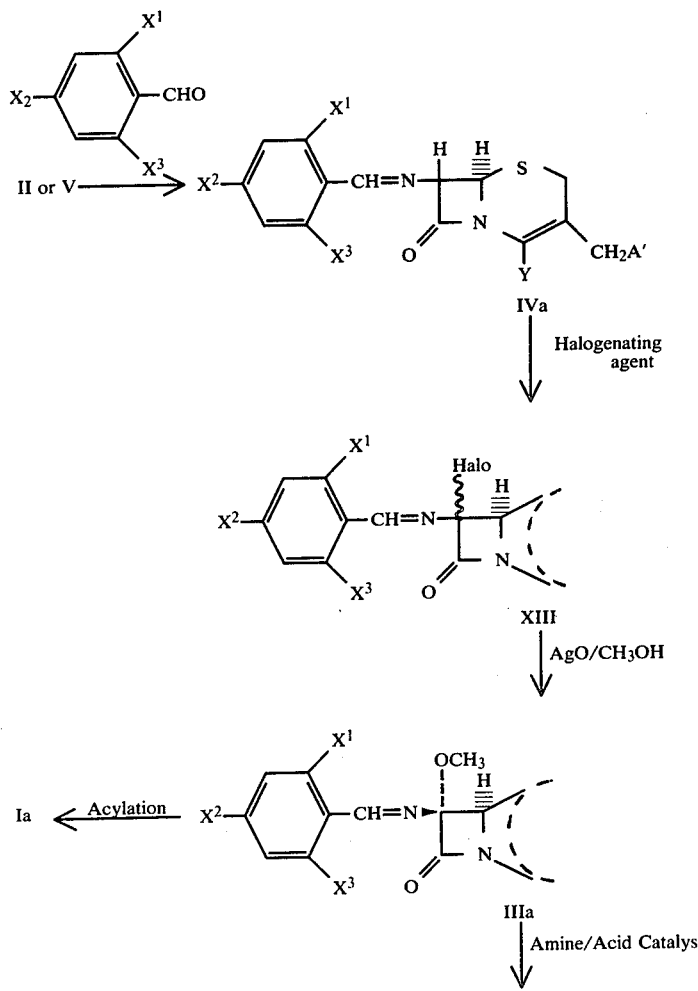

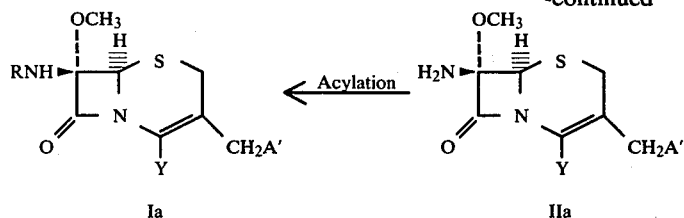

Flow Sheet III 7α-CH₃

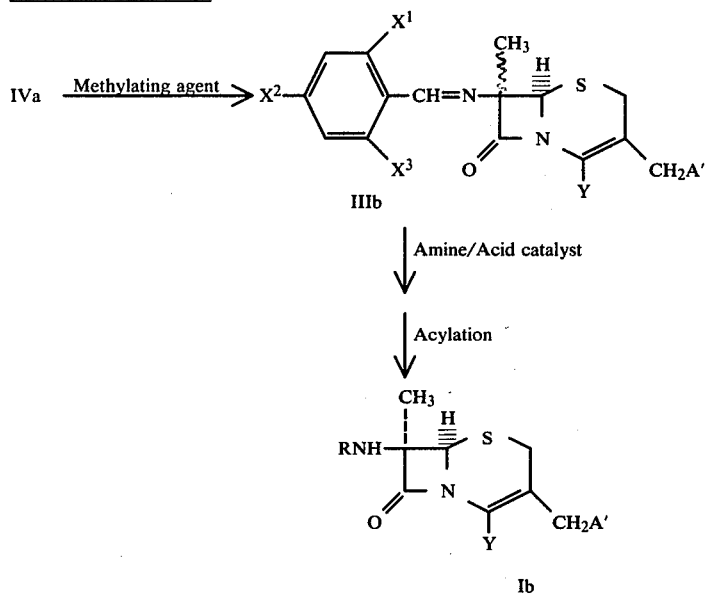

Flow Sheet IV 7α-Alkylthio

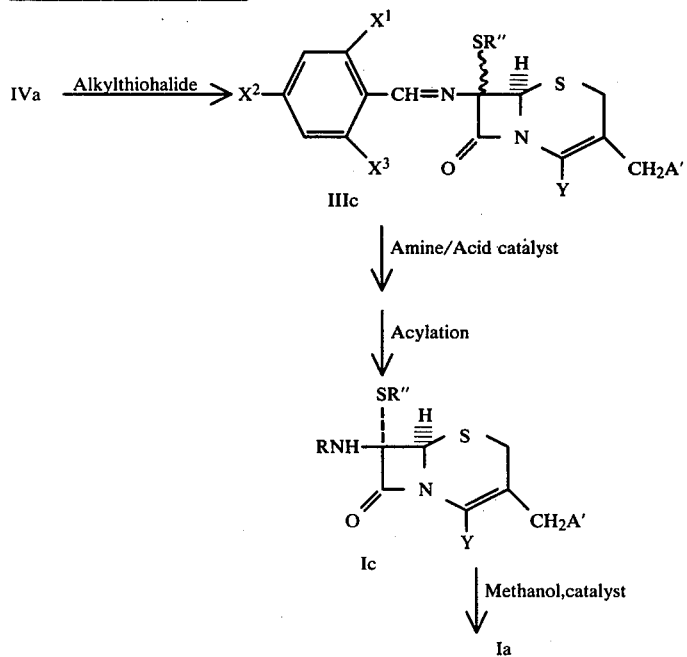

In this process, an ester of methylene diphosphonic acid, an ester of methylene sulfophosphonic acid or an ester of methylene sulfonamidophosphonic acid is converted to its corresponding α-diazo intermediate by reaction with tosyl azide. The 2-diazo compound is then reduced to afford the corresponding α-amino intermediate (X). The α-aminomethylene diphosphonates may also be prepared by treating dibenzylamine with formic acid and acetic anhydride to afford N-formyl-dibenzylamine which is treated first with oxalyl chloride and then with a trialkyl phosphite such as trimethylphosphite to afford the tetraalkyl N,N-dibenzylaminomethylenediphosphonate which is catalytically reduced to afford the desired α-aminomethylenediphosphonate.

The α-amino compound (X) is next reacted with a thioformate ester to produce the corresponding N-thioformamido ester (IX). Various esters of the above-mentioned acids can be utilized as starting materials in the above-shown process. Thus, various esters of the phosphono group include, for example, the di-lower alkyl esters wherein R⁴ is lower alkyl of 1–4 carbon atoms such as methyl, ethyl, n-propyl, isopropyl, and n-butyl, esters of the aryl esters wherein R⁴ is phenyl or p-nitrophenyl. Various esters of the sulfo group include the lower alkyl esters, substituted lower alkyl esters, benzyl and substituted benzyl esters, such as p-nitrobenzyl or p-methoxybenzyl esters, aryl or diaryl esters, phenacyl esters and the like.

Examples of suitable starting materials include tetramethyl methylenediphosphonate, tetraethyl methylenediphosphonate, tetraisopropyl methylenediphosphonoate, tetraphenyl methylenediphosphonate, tetra-(p-nitrobenzyl) methylenediphosphonate, diethyl sulfamoylmethylphosphonate, diphenyl sulfamoylmethylphosphonate, di-n-butyl sulfamoylmethylphosphonate, dimethyl methoxysulfonylmethylphosphonate, dimethyl p-methoxybenzylsulfonylmethylphosphonate, diphenyl trichloroethoxysulfonylmethylphosphonate, di-n-propyl phenoxysulfonylmethylphosphonate, dimethyl benzhydryloxysulfonylmethylphosphonate, diethyl methoxymethoxysulfonylmethylphosphonate, dibutyl phenacyloxysulfonylmethylphosphonate, diethyl sulfomethylphosphonate and the like.

The conversion of compound X to the corresponding thioformamido derivative (IX) is carried out by reacting the compound (X) with a lower alkyl thioformate ($C_1$–$C_6$). The reaction is conveniently carried out by reaction with ethyl thioformate at 0° C. Generally, it is preferred to carry out the reaction in an inert solvent media such as benzene, carbon tetrachloride, methylene chloride or hexane. Alternatively, the reaction is carried out in the presence of liquid hydrogen sulfide at room temperature. After completion of the reaction, the solvent is evaporated to afford the desired product, IX.

The next step comprises reacting the intermediate product IX with a substituted acetone of the general formula A'CH₂COCH₂X wherein A' is as defined below and X is halo such as bromo, iodo or chloro, in the presence of an acid scavenger to produce the corresponding S-acetonyl or S-substituted acetonyl compound VIII. Thus, the reaction is conveniently carried out by reacting the intermediate product IX with the halo substituted acetone in the presence of about one equivalent of an inorganic base such as an alkali metal carbonate, for example, potassium carbonate at room temperature. After the reaction is complete, the product (VIII) is conveniently isolated by filtering the reaction mixture and evaporating the filtrate to dryness.

The intermediate S-acetonyl or S-substituted acetonyl compound (VIII) upon reaction with a base such as an alkali metal carbonate or hydride is converted to the corresponding thiazine compound (VII). Alternatively, when the condensation of the thioformamido derivative (IX) and the substituted acetone is carried out in the presence of more than about one equivalent of the base, the product is essentially all in the form of the thiazine (VII). Thus, this compound is produced almost exclusively when two or more equivalents of potassium carbonate are used in the condensation reaction.

A' in the formula of the substituted acetone, A'CH₂COCH₂X, represents hydrogen, a lower alkanoyl group such as acetoxy, isobutyryloxy and the like, carbamoyloxy, N-substituted carbamoyloxy such as N-trichloroethyl carbamoyloxy and the like, N,N-disubstituted carbamoyloxy such as N,N-di-p-nitrobenzylcarbamoyloxy and the like, halo such as bromo, chloro and fluoro, lower alkoxy, such as methoxy and the like, aryloxy such as phenoxy and the like, aralkyloxy such as benzyloxy and the like or substituted aralkyloxy such as 4-methoxybenzyloxy, 4-nitrobenzyloxy and the like or a lower alkoxy lower alkoxy group such as methoxymethoxy and the like.

Examples of these substituted acetones that might be mentioned are chloroacetone, 1-chloro-3-acetoxyacetone, 1,3-dichloroacetone, 1-chloro-3-carbamoyloxyacetone, 1-chloro-3-(N-trichloroethylcarbamoyloxy)acetone, 1-chloro-3-phenoxyacetone, 1-chloro-3-(p-methoxybenzyloxy)acetone, 1-chloro-3-benzyloxyacetone, 1-chloro-3-(p-nitrobenzyloxy)acetone, 1-bromo-3-methoxymethoxyacetone and 1-chloro-3-methoxyacetone. These substituted acetone compounds are known compounds or can be readily prepared pursuant to methods known in the art. Thus, chloroacetone and 1-chloro-3-acetoxyacetone can be prepared by known methods. The 1-chloro-3-carbamoyloxyacetone is prepared by converting 1-chloro-3-acetoxyacetone to the dimethylketal, hydrolyzing this product to the 3-hydroxy compound, and reacting this product with sodium cyanate and trifluoroacetic acid in methylene chloride.

The intermediate thiazine compound VII or the mixture of this product with the acetonyl compound VIII is then reacted with azidoacetyl chloride in the presence of an acid scavenger to afford the 7α-azido compound, VI. The reaction is preferably carried out at low temperatures, for example, at about 0° C., and in the presence of a sufficient amount of base such as a tertiary amine which serves as an acid scavenger and, in addition, catalyzes the cyclization of the intermediate compound.

Alternatively, the desired 7α-azido compound VI is obtained by reacting a mixture of the acyclic compound VIII and the cyclic VII compound with the azidoacetyl chloride under the described conditions. When the acyclic compound VIII is reacted a cyclic intermediate compound of the structure:

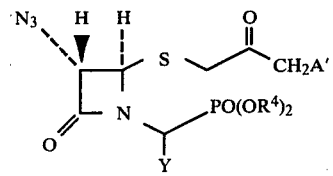

is formed, and this product is then cyclized under the reaction conditions to the desired 7α-azido compound VI.

In this series of reactions a phosphonate group is employed as the activating group which group is cleaved in the preparation of the thiazine intermediate. In place the phosphonate activating group in the above-identified starting compounds there may be employed other activating groups such as methyl sulfinyl, dimethylsulfonium and trimethylsilyl.

The 7α-azido compound VI is then reduced to obtain the corresponding 7α-amino compound V. This reduction is conveniently effected with hydrogen disulfide in the presence of triethylamine, or with hydrogen in the presence of a noble metal catalyst such as platinum oxide, palladium on charcoal, ruthenium, rhodium and the like at a temperature in the range of from about 0° C. to about 50° C. Suitable solvents for this reaction include benzene, dioxane, ethyl acetate or ethanol.

The 7α-amino compound, V, is then reacted with an aromatic aldehyde in which $X^1$, $X^2$, and $X^3$ are the same or different radicals selected from hydrogen, nitro, halo, hydroxy, cyano or a carboxy derivative such as an ester or an amide.

Other carbonyl containing compounds, e.g., aldehydes and ketones such as acetone, hexafluoroacetone, or chloral which will form stable imino derivatives will also be operable in this invention. Also, polycyclic aromatic aldehydes can be used, i.e., having 2–3 fused ring nuclei.

The 7α-amino compound, V, and the aromatic aldehyde are mixed together in approximately equimolar amounts in an inert solvent. Suitable solvents include ethanol, dioxane, acetonitrile, dimethylformamide, dimethylsulfoxide, benzene, toluene, methylene chloride, chloroform and the like. The reaction proceeds readily at a temperature of the particular solvent employed. This reaction is an equilibrium reaction and the water formed is removed by any of a number of methods including azeotropic distillation, molecular sieves, chemical entrapment using potassium carbonate, magnesium sulfate and the like or borate esters. The particular method employed to remove the water is dependent upon the exact parameters of the reaction. The reaction is terminated by filtration and evaporation of the solvent to afford the 7α-imino compound IV.

The 7α-imino derivative IV is then dissolved in an inert aprotic solvent, preferably tetrahydrofuran. Then an equivalent or more of a strong base is added. The strong base functions as an "activating agent" and can be either organic or inorganic. Most suitable are the lithium alkyls and lithium aryls, for example, lithium alkyls having 1–4 carbon atoms such as t-butyl lithium, n-butyl lithium or phenyl lithium. Sodium hydride, potassium tert-butoxide and lithium trimethylsilyl amide are also suitable.

The activating agent is added to the solution of compound IV at a low temperation ($-100°$ to $0°$ C. and preferably $-100°$ to $-60°$ C.), preferably under an inert atmosphere. The amount of activating agent employed is from 1–3 eqivalent weights.

Following addition of the strong base (phenyl lithium is particularly preferred), another solvent, which is a dipolar aprotic solvent, is added to the mixture. By the term "dipolar aprotic solvent" is meant a strongly dipolar solvent having no acidic protons. Preferred solvents include dimethylformamide, dimethylsulfoxide, hexamethylphosphoramide, N-methylpyrrolidone or dimethylacetamide.

The solvent and the co-solvent are preferably employed sequentially, as described, although this is not critical; the solvent, co-solvent, and strong base can operably be added in any order to the 7α-imino compound.

Following the addition of the solvent, base and co-solvent to the 7α-imino compound, a molecular excess (from 1–5 equivalents) of an acid is added in one portion as quickly as possible. The acid employed can be any organic or inorganic acid; the only limitation is that it not affect the cephalosporin ring. Preferably, a lower carboxylic acid is employed having 1–5 carbon atoms and preferably, acetic acid. The acid can be added as an aqueous solution or in the presence of water. The acid serves as a source of protons which exist as solvated protons in the reaction solution.

After the acid has been added, the compound III, the 7β-imino compound, is present in the reaction mixture and can be isolated using standard purification techniques.

The 7β-imino compound III is then converted to the 7β-amino compound II by the reaction of compound III with an amine in the presence of an acid catalyst. The amine employed can be aniline, hydrazine or hydrazine derivatives such as phenylhydrazine, 2,4-dinitrophenylhydrazine and the like. The acid catalyst can be any commonly used strong inorganic or organic acid such as hydrochloric acid or p-toluenesulfonic acid. A preferred amine is aniline as its hydrochloride salt which serves as both acid and amine. Another preferred amine is 2,4-dinitrophenylhydrazine with p-toluenesulfonic acid. The reaction conditions of the conversion are such that no undesired hydrolysis or ring damage occurs. The reaction is preferably conducted in a lower alkanol solvent ($C_{1-5}$) such as methanol, ethanol and the like, although other solvents including dimethoxyethane o-dimethylformamide may be used. The reaction is conveniently conducted at ambient temperature. The relative amounts of acid and amine employed depend on the specific aldehyde and amine used, since the conversion to the amine is an equilibrium reaction. The choices of the amounts of the reagents is within the skill of one in the art.

The above reaction conditions are suitable for removal of difficult hydrolyzable Schiff's bases such as those with strong electronegative groups. When the Schiff's base is formed with benzaldehyde, the following methods can also be used to regenerate the amine.

The 7β-imino compound can be dissolved in ether, and then added slowly to an ether solutions of p-toluenesulfonic acid mono-hydrate. No additional amine is needed. The formed salt will either crystalline or oil out of solution. Following removal of the ether the tosylate salt is treated with aqueous pH 8 solution and extracted to recover the desired 7β-amino compound.

An alternate route involves treatment of the 7β-imino compound with pH 2–2.5 buffer for 5–15 minutes, extracting with ether to remove the free aldehyde, then neutralizing to pH 8 and extracting to recover the 7β-amino compound.

When the 7-methoxy compounds are desired, the 7α-amino compound (V) or the 7β-amino compound (II) are treated as depicted in Flow Sheet II with an aromatic aldehyde, as described above, to afford the correspondingly substituted 7α or 7β-imino compound (IVa). This imino compound (IVa) is treated with a strong base in the manner described above, in the conversion of the 7α-imino compound to the 7β-imino compound to afford an activated intermediate.

The activated intermediate is not isolated but treated directly with a halogenating agent such as N-bromosuccinimide, N-bromoacetamide, bromide, tert-butyl hypochlorite, perchloromethyl hypochlorite and the like, to afford the 7-imino-7-halo compound (XIII, supra) which upon treatment with methanol in the presence of a base such as silver oxide, barium oxide, calcium oxide, barium oxide, calcium oxide, cuprous oxide or triethylamine affords the 7β-imino-7α-methoxy compound (IIIa) which can be directly acylated or can be treated with an amine in the presence of an acid catalyst as described above to afford the 7β-amino-7α-methoxy compound (IIa, infra).

The process for preparing the 7-acylamido compounds (I, supra) comprises treating the 7-amino or 7-substituted amino compound (II, infra) with an acylating agent, for example, an acyl halide or acyl anhydride such as an aliphatic, aromatic, heterocyclic, aralphatic or heterocyclic aliphatic carboxylic acid halide or anhydride. Other acylating agents may also be employed, for example, a mixed acid anhydride with other carboxylic acids particularly lower alkyl esters of carboxylic acids; also, carboxylic acids in the presence of a carbodiimide such as 1,3dicyclohexylcarbodiimide, an activated ester of a carboxylic acid such as the p-nitrobenzyl ester of by enzymatic acylation.

When an imino compound is employed increased yields are obtained with the imino compound is first treated with a metal catalyst. This first comprises dissolving the imino compound (III) in an inert solvent such as tetrahydrofuran, dimethylsulfoxide, dioxane, dimethylformamide, methanol, ethanol, methylene chloride or chloroform. A small amount of water is then added such that the solvent to water ratio is about 5–6:1. The metal catalyst is then added and the reaction mixture stirred at ambient temperature for 1–5 hours. The solvent may be removed of the acylating agent added directly to the reaction mixture. The catalyst is of the formula $ML_n$ where M is a metal such as palladium, platinum, nickel, ruthenium, rhodium, cobalt or iron; L is the ligand such as halo, carbonyl, cyclopentadienyl, phenylcyano and the like; and n is an integer which is equal to the valence requirements. Palladium chloride ($PdCl_2$) is the preferred catalyst.

The acylation reaction may be conducted at a temperature in the range of from about $-20°$ C. to about $100°$ C. but is preferably conducted at a temperature in the range of from $0°$ C. to $25°$ C. Any solvent in which the reactants are soluble and substantially inert may be employed, for example, hydrocarbons such as benzene, toluene, and the like or tertiary amines, for example, trialkylamines and heterocyclic amines such as trimethylamine, pyridine and the like, also methylene chloride, chloroform, ethylacetate or diethylether may be employed. The reaction is conducted for a period of time of from about five minutes to a maximum of three hours, but in general, a reaction time of about 0.5 to about one hour is sufficient.

The processes in Flow Sheets III and IV both start with the imino derivative IVa (Flow Sheet II). This imino derivative is then substituted with the chosen reagent, a methylating agent to yield 7α-methyl compounds, or an alkylthiohalide to yield 7α-alkylthio compounds.

The reaction with this reagent takes place in the presence of an inert solvent, such as tetrahydrofuran, dimethylformamide, and others, and in the additional presence of an activating agent which is an organic or inorganic base.

The activating agent can be any of a number of organic or inorganic bases. Tertiary (loweralkyl) amines are suitable, such as triethylamine, diisopropyl ethylamine; lower alkyl is used as having 1-4 carbon atoms and can be the same or different. Pyridine is also used. Lithium alkyls and lithium aryls having 1-4 carbon atoms, e.g., t-butyl lithium or phenyl lithium, could be used. Sodium hydride is also suitable, $LiN(iPr)_2$ and KOtBu may be used.

The activating agent is added to the solution of compound IVa at a low temperature ($-100$ to $0°$ C. and preferably $-100$ to $-60°$ C.) and under an inert atmosphere. The amount of activating agent employed is sufficient to produce a strong color change in the solution. The color is an indicator that the activated form of compound IVa is present.

The activated compound IVa is not isolated, but the chosen reagent is added directly to the reaction mixture.

In the case of compounds having a 7α-methyl substituent, methyl sulfate or methyl halide, especially methyl iodide are used to react with IVa. In the case of the 7α-loweralkyl thio substituent, the reactant is a loweralkane sulfinyl halide, e.g., methyl sulfenyl halide, or a loweralkyl methanethiolsulfonate, e.g., methyl methane thio sulfonate.

The chosen reagent is added in an amount approximately to the moles of the activated compound IVa. The reaction proceeds immediately, as evidenced by a color change. The reaction mixture is than permitted to warm up to temperatures ranging from between $0°$ C. to ambient temperatures, to quench.

Following the preparation of the intermediates IIIb or IIIc, these later are treated with amine/acid catalyst and acylated as described above yield the acylated products Ib or Ic.

Additionally, in the case of Ic, the compound can be further treated with methanol in the presence of a thallium salt catalyst, e.g., thallium trinitrate to effect preparation of the 7α-methoxy compound Ia.

The compounds described in the Flow Sheets, since they result from a total synthesis procedure, are racemic mixtures of both d- and l-forms. The separation of the two optically active components can be conveniently done when the compound of Formulas II is obtained. Alternatively, the compound of Formulas II can be acylated to yield the d,l-7β-acylamino cephalosporins, I, and then separated using readily available processes. For example, resolution can be accomplished by reaction with an optically active base, separation of the resulting diastereomers, and reconversion of the diastereomers to the free acid or a salt thereof.

The 3-acetoxy group may also be converted to other analogs i.e., where $A^1$ is pyridinium or a 5-membered heterocyclicthio by replacing the actoxy group of I with nitrogen or sulfur nucleophiles. Many nitrogen and sulfur nucleophiles are well known in the cephalosporin art and the following examples are merely illustrative of the type of compound which may be employed; for example, a tertiary amine such as pyridinium and the like, a 5-membered heterocyclic thiol such as 5-methyl-1,3,4-thiadiazolyl-2-thiol, N-methyltetrazolylthiol and the like.

The final 7β-acylamino products, I, are valuable antibacterial agents useful against gram-positive and gram-negative bacteria. This activity includes effectiveness against many bacteria, including in vivo on *Escherichia coli, Proteus vulgaris* and Bacillus subtilis. Specific bactericidal activity is depenent upon the exact structure of the final product; not all compounds are active against all organisms.

The final active antibiotic agents can be used to combat bacterial infections in animals or humans. They can be employed in dosages and administrative forms similar to that employed for commercially available cephalosporins and penicillins. Exact dose levels and modes of administration can be readily determined by one skilled in the art. Generally, between 0.1–500 mg.kg. body weight can be employed go give effective antibacterial control.

The nomenclature used in this application is as follows:

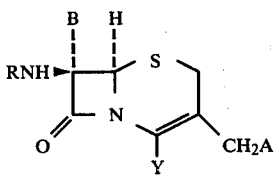

is called 3-substituted methyl-7β-acylamino-7α-β-3-cephem-4-Y where Y is a phosphonic acid product, a sulfonic acid radical or a sulfonamido radical or a salt, ester or amide thereof.

In Formula I, the dotted line connecting the two substituents (B or H) to the ring indicate that the substituents are down from the plane of the β-lactam ring; the broad line connecting the nitrogen indicates that it is up from the plane of the ring.

There is another possible steric configuration for a cephalosporin, which is:

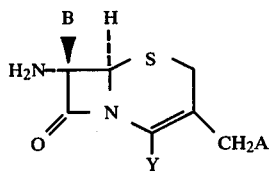

In this formula, the nitrogen and the hydrogen at position 6 is α, or down from the ring; the hydrogen at position 7 is β, or up from the ring. This type of configuration is termed "epi" cephalosporin.

It should be noted that it is unnecessary to specify the configuration of both substituents on the 7-carbon; if the nitrogen configuration is indicated, the other substituent, i.e., the hydrogen, is obviously the other configuration.

EXAMPLE 1

Disodium d,
1-3-acetoxymethyl-7β-(2-thienylacetamido)-3-cephem-4-phosphonate

Step A: Tetramethyl diazomethylenediphosphonate

To potassium t-butoxide (360 mg.) in benzene (10 ml.) in an ice bath (10°–15° C.) under an atmosphere of nitrogen is added tetramethyl methylene diphosphonate (696 mg.) in 2 ml. of dry dimethylsulfoxide. The solution is stirred for 15 minutes at 10°–15° C., then tosyl azide (600 mg./1 ml. of dimethylsulfoxide) is added. The reaction mixture is stirred at room temperature for two hours. The reaction mixture is treated with cold water. The aqueous layer is separted and extracted with methylene chloride. The organic layers are dried over magnesium sulfate, filtered and evaporated under reduced pressure to yield tetramethyl diazomethylenediphosphonate.

Step B: Tetramethyl α-aminomethylenediphosphonate

A mixture of tetramethyl diazomethylenediphosphonate (100 mg.), palladium (5% on crbon, 100 mg.) and glacial acetic acid (5.0 ml.) is hydrogenated at 40 p.s.i. overnight at room temperature. The catalyst is removed by filtration through supercel and the filtrate evaporated under reduced pressure to yield tetramethyl α-aminomethylene diphosphonate.

Step C: Tetramethyl α-thioformamido-methylenediphosphonate

To a thick-walled, glass tube are added tetramethyl α-amino-methylenediphosphonate (3.38 g.) and ethyl thionoformate (7.5 ml.). The mixture is cooled to −78° under nitrogen and hydrogen sulfide (ca. 4 ml.) is condensed into it. The tube is then sealed, and the mixture is allowed to warm to room temperature and kept at room temperature overnight. The tube is cooled to −78° and opened. The hydrogen sulfide is allowed to evaporate with warming to room temperature. The residue is filtered to remove sulfur and the filtrate concentrated in vacuo. Chromatography of the residue on silica gel (180 g.) using 5% methanol in chloroform as eluting solvent affords tetramethyl α-thioformamido-methylenediphosphonate (1.26 g.) as white crystals:

ir (nujol) 3.20, 7.00. 8.11, and 9.75μ; nmr (CDCl₃)δ3.74 (m,12, OCH₃), 6.19(d of t,l,J =10Hz and J −21 Hz, CH), 9.55(d,l,J - 6Hz, CSH), and 10.2(m,1,NH).

Step D: 3-Acetoxy-2-oxo-propyl N-tetramethyldiphosphonomethyl-thioformimidate

A mixture of tetramethyl α-thioformamido-methylenedipnosphonate (600 mg.), anhydrous powdered potassium carbonate (287 mg.), 1-acetoxy-3-chloro-2-propanone (300 mg.), and acetone (70 ml.) is stirred under a nitrogen atmosphere for 17 hours at room temperature. The mixture is filtered and the salts washed with more actone. The combined filtrate and washings is evaporated in vacuo to have crude 3-acetoxy-2-oxo-propyl N-tetramethyldiphosphonomethyl-thioformimidate (862 mg.) as an oil:

nmr (CDCl₃) 2.13(s,3,OCOCH₃), 3.82(m,14,OCH₃ and SCH₂), 4.35(d of t,l,J =3Hz and J =2OHz,CH), 4.90(S,Z,CH₂OAc), and 8.28(t,l,J =3Hz, N=CH).

Step E: Dimethyl 5-acetoxymethyl-6H-1,3-thiazine-4-phosphonate

Sodium hydride (81 mg. of a 57% dispersion in mineral oil, previously washed with petroleum ether) is added to a solution of 3-acetoxy-2-oxo-prepyl N-tetramethyldiphosphonomethyl-thioformimidate (862 mg.) in anhydrous dimethoxyethane (6 ml.). The resulting mixture is stirred under a nitrogen atmosphere for 5 minutes at room temperature and 5 minutes at 50°. The mixture is then diluted with benzene, washed with pH7 phosphate buffer, dried over magnesium sulfate, filtered, and concentrated under reduced pressure. The residue (177 mg.) is crude dimethyl 5-acetoxymethyl-6H-1,3thiazine-4-phosphonate:

nmr (CDCl₃)δ2.11 (s,3,OCOCH₃), 3.31(m,2,SCH₂), 3.80(m,6,OCH₃), 5.35(d,2J =3Hz, CH₂OAc), and 8.36(m,1,N=CH).

Step F: Dimethyl d,1-7α-azido-3-acetoxymethyl-3-cephem-4-phosphonate

The crude thiazine (177 mg.) from the previous example is dissolved in anhydrous methylene chloride and the solution is cooled to −78° under nitrogen. Triethylamine (92μl.) is added followed by a solution of azidoacetyl chloride (59μI.) in methylene chloride (1 ml.) over a period of 5 minutes. The resulting solution is allowed slowly to warm to room temperature, and then diluted with more methylene chloride and washed with water. The solution is dried with magnesium sulfate, filtered, and concentrated in vacuo to a dark oil. This material is chromatographed on silica gel (10 g.). Elution with 10% acetone in chloroform affords dimethyl d,1-7α-azido-3-acetoxymethyl-3-cephem-4-carboxylate:

ir (CHCl₃) 4.71, 5.59, 5.74, 8.1, and 9.7μ; nmr (CDCL₃)δ2.12(s,3,OCOCH₃), 3.43(m, 2,SCH₂), 3.88(m,6,OCH₃), 4.60(s,2,CH₂OAc), and 5.30 (m,2, H6 and H7).

Step G: Dimeethyl d,1-3-acetoxymethyl-7α-amino-3-cephem-4-phosphonate

A mixture of dimethyl d,1-3-acetoxymethyl-7α-azido-3-cephem-4-phosphonate (485 mg.), platinum oxide (450 mg.) and benzene (50 ml.) is hydrogenated at 40 p.s.i. for 60 minutes. The catalyst is removed by filtration through a Supercel filter cake and the filtrate is evaporated under reduced pressure to yield dimethyl d,1-3-acetoxymethyl-7α-amino-3-cephem-4-phosphonate.

Step H: Dimethyl d,1-3-acetoxymethyl-7α-(p-nitrobenzylideneamino)-3-cephem-4-phosphonate A mixture of dimethyl d, 1-3-acetoxymethyl-7α-amino-3-cephem-4-phosphonate (403 mg., 1.2 mmol.), p-nitrobenzaldehyde (181 mg., 1.2 mmol.), magnesium sulfate (3.0 g.) and methylene chloride (30 ml.) is stirred for two hours at room temperature. The mixture is filtered and the filtrate is evaporated under reduced pressure to yield dimethyl d,1-3-acetoxymethyl-7α-(p-nitrobenzylideneamino)-3-cephem-4-phosphonate.

Step I: Dimethyl d,1-3-acetoxymethyl-7β-(p-nitrobenzylideneamino)-3-cephem-4-phosphonate Anhydrous tetrahydrofuran (20 ml.) and dimethyl d,1-3-acetoxymethyl-7α-(p-nitrobenzylideneamino)-3-cephem-4-phosphonate (562 mg., 1.2 mmol.) are stirred at −78° C. under an atmosphere of nitrogen. Phenyllithium (0.52 ml. of a 2.3 M solution in 7:3 benzene-ether) is added, forming the deep blue anion. Dimethylformamide (25 ml.) is added dropwise over a period of 15 minutes and after one more minute at −78° C. a solution of water (216 mg.) and acetic acid (180 mg.) in tetrahydroguran (20 ml.) is added. The reaction mixture is allowed to warm to room temperature, then diluted with benzene (400 ml.) and washed with water (6 ×200 ml.). The second wash is acidified with pH2 phosphate buffer, and the fifth basified with pH9 buffer. The benzene solution is dried over magnesium sulfate, filtered and evaporated in vacuo to give a mixture of dimethyl d,1-3-acetoxymethyl-7β-(p-nitrobenzylideneamino)-3-cephem-4-phosphonate and dimethyl d,1-3-acetoxymethyl-7α-(p-nitrobenzylideneamino)-3-cephem-4-phosphonate.

Step J: Dimethyl d,1-3-acetoxymethyl-7β-amino-3-cephem-4-phosphonate

The mixture of dimethyl d,1-3-acetoxymethyl-7-(p-nitrobenzylideneamino)-3-cephem-4-carboxylates (548 mg., 1.17 mmol.) obtained in the previous example is dissolved in chloroform (4 ml.) and added to a solution of 2,4-di-nitrophenylhydrazine p-toluenesulfonic acid in ethanol (prepared from 232 mg. of 2,4-dinitrophenylhydrazine and 223 mg. of toluenesulfonic acid monohydrate stirred in 35 ml. of ethanol for 45 minutes). The reaction mixture is stirred for 30 minutes, filtered and the filtrate is evaporated in vacuo. The residue is treated with aqueous pH9 phosphate buffer and extracted three times with ether. The combined extracts are dried over magnesium sulfate, filtered and evaporated in vacuo to provide a mixture of dimethyl d,1-3-acetoxymethyl-7β-amino-3-cephem-4-phosphonate and dimethyl d,1-3-acetoxymethyl-7α-amino-3-cephem-4-phosphonate.

Step K: Dimethyl d,1-3-acetoxymethyl-7β-(2-thienylacetamido)-3-cephem-4-phosphonate and dimethyl d,1-3-acetoxymethyl-7α-(2-thienylacetamido)-3-cephem-4-phosphonate A mixture (319 mg., 0.95 mmol.) of dimethyl d,1-3-acetoxymethyl-7β-amino-3-cephem-4-phosphonate and dimethyl d,1-3-acetoxymethyl-7α-amino-3-cephem-4-phosphonate is dissolved in anhydrous methylene chloride (7 ml.). The resulting solution is stirred at 0 C. and under a nitrogen atmosphere. Pyridine (350 ml.) is added followed by a solution of thienylacetyl chloride (153 mg., 0.95 mmol.) in methylene chloride (3 ml.). After being stirred for 15 minutes at 0° C. the reaction mixture is diluted with benzene (60 ml.). The benzene solution is washed with pH2 phosphate buffer, water, pH9 phosphate buffer, water and saturated brine, dried over magnesium sulfate, filtered and evaporated in vacuo to an oil. Chromatography of the crude product on silica gel (25 g.) using an ethyl acetatebenzene gradient to elute the products affords dimethyl d,1-3-acetoxymethyl-7β-(2-thienylacetamido)-3-cephem-4-phosphonate and dimethyl d,1-3-acetoxymethyl-7α-(2-thienylacetamido)-3-cephem-4-phosphate.

Step L: Disodium d,1-3-acetoxymethyl-7β-(2-thienylacetamido)-3-cephem-4-phosphonate A solution of dimethyl d,1-3-acetoxymethyl-7β-(2-thienylacetamido)-3-cephem-4-phosphonate (138 mg., 0.3 mmol.) and trimethylchlorosilane (130 mg., 1.2 mmol.) in anhydrous tetrahydrofuran (0.2 ml.) is heated in a sealed tube for 18 hours at 90° C. The tube is opened and the contents evaporated in vacuo to a residue which is stirred for three hours with water (10 ml.). The aqueous mixture is brought to pH8.2 with dilute sodium hydroxide, extracted with chloroform and lyophilized to yield disodium d,1-3-acetoxymethyl-7β-(2-thienylacetamido)-3-cephem-4-phosphonate.

Alternate Preparation of Tetraalkyl α-Aminomethylenediphosphonates

Step A: N-Formyl-dibenzylamine

To an ice-cold and vigorously stirred solution of dibenzylamine (918 g.) in 98% formic acid (105 ml.) is added dropwise, over 45 minutes, acetic anhydride (35 ml.). The resulting mixture is stirred for one hour at room temperature, then diluted with ice water (40 ml.) and kept overnight at 15° C. The solution is evaporated in vacuo to dryness and the residue extracted with ether. The ethereal solution is washed with water, dried over magnesium sulfate, filtered, and evaporated in vacuo to yield N-formyl-dibenzylamine (9.9 g.) as a white solid, m.p. 53°–54.5° C.

ir (CHCl₃) 6.01, 7.01, 7.18, and 10.22μ. nmr (CDCl₃)tau 5.76 (s,2,C$\underline{H}$₂), 5.60 (s,2,C$\underline{H}$₂), 2.73 (m,10,Ar$\underline{H}$), and 1.56 (s,1,$\underline{H}$CO).

Step B: Tetramethyl N,N-dibenzyl-aminomethylene diphosphonate

A solution of oxalyl chloride (2.52 g.) in methylene chloride (2 ml.) is added dropwise over 20 minutes to an ice-cold, stirring solution of N-formyldibenzylamine (4.5 g.) in methylene chloride (8 ml.). The reaction mixture is stirred an additional hour at 0°–5° C., then cooled to −40° C. A solution of trimethyl phosphite (4.96 g.) in methylene chloride (4 ml.) is added dropwise over 20 minutes. The cooling bath is removed and the mixture is kept overnight at room temperature. Evaporation of the solvent in vacuo leaves crude tetramethyl N,N-dibenzyl-aminomethylene diphosphonate (4.6 g.). A 0.50 g. portion of the above product is chromatographed on silica gel (30 g.). Elution with 3% methanol in chloroform gives pure tetramethyl N,N-dibenzyl-aminomethylene diphosphonate (0.47 g.) as an oil.

ir (CHCl$_3$) 6.79, 6.88, 7.28, 8.1, and 9.6μ. nmr (CDCl$_3$) tau 6.38 (t,1,J=26Hz, C$\underline{H}$), 6.36–6.–6(m, 1-2,OC$\underline{H}_3$), 5.93 (s,4,C$\underline{H}_2$), and 2.60 (m,10, Ar$\underline{H}$

Step C: Tetramethyl α-aminomethylene diphosphonate

A mixture of tetramethyl N,N-dibenzyl-aminomethylene diphosphonate (125 mg.), 10% palladium on charcoal (125 mg.), and methanol (8 ml.) was hydrogenated at 40 p.s.i. for 25 hours. The mixture was filtered through a pad of super cel and the filtrate evaporated in vacuo to give tetramethyl α-aminomethylene diphosphonate (66 mg.).

nmr (CDCl$_3$) tau 8.15 (br s,2,NH$_2$), 6.48 (t,1,J=21Hz,CH), and 6.25–5.98 (m,12,OCH$_3$).

EXAMPLE 2

Disodium d,1-3-acetoxymethyl-7β-(2-thienylacetamido) 3-cephem-4-phosphonate

Step A: N,N-dibenzyl-α-amino-methylenediphosphonic acid

A solution of tetramethyl N,N-dibenzyl- -aminomethylenediphosphonate (4.00 g.) in trimethylchlorosilane (100 ml.) is heated to reflux for 3 days in an oil bath maintained at 95°. The vapors are condensed by means of a Dry Ice-acetone trap. After cooling to room temperature, the reaction mixture is diluted with water (300 ml.) and shaken vigorously. The mixture is extracted with chloroform (3 ×150 ml.). The aqueous layer is separated and evaporated to dryness, affording N,N-dibenzyl-α-amino-methylenediphosphonic acid as a white solid.

Step B: Tetrachloro N,N-dibenzyl-α-amino-methylenediphosphoridate

Phosphorus pentchloride (8.34 g.) is added to a solution of N,N-dibenzyl-α-amino-methylenediphosphonic acid (3.71 g.) in phosphorus oxychloride (40 ml.). The reaction mixture is heated for 1 hour in an oil bath maintained at 100°. The phosphorus oxychloride is removed in vacuo and the residue several times stripped with anhydrous benzene to yield tetrachloro N,N-dibenzyl-α-amino-methylenediphosphoridate.

Step C: Tetra-t-butyl N,N-dibenzyl-α-amino-methylenediphosphonate

A solution of tetrachloro N,N-dibenzyl-α-amino-methylenediphosphoridate (4.40 g.) in anhydrous benzene (40 ml.) is added dropwise over 20 minutes to an ice-cold, stirring solution of t-butanol (2.96 g.) and pyridine (3.16 g.) in anhydrous benzene (200 ml.). After stirring an additional one hour at room temperature, the reaction mixture is heated at reflux for 15 minutes. The mixture is cooled, filtered to remove pyridinium hydrochloride, and the filtrate washed with water. The benzene solution is dried over magnesium sulfate, filtered, and evaporated in vacuo to yield tetra-t-butyl N,N-dibenzyl-α-amino-methylenediphosphonate.

Step D: Tetra-t-butyl α-amino-methylene-diphosphonate

A mixture of tetra-t-butyl N,N-dibenzyl-α-amino-methylenediphosphonate (12.0 G.), 10% palladium on carbon (4.0 g.), and 25% aqueous dioxane (500 ml.) is hydrogenated at 40 p.s.i. for 4 hours. The catalyst is removed by filtration through a pad of diatomaceous earth, which is washed with more dioxane. The filtrate and washings are concentrated in vacuo to ca. 50 ml. and extracted with four portions of chloroform. The extracts are dried with magnesium sulfate, filtered, and evaporated in vacuo to yield tetra-t-butyl α-amino-methylenediphosphonate.

Step E: Tetra-t-butyl α-thioformamido-methylenediphosphonate

A mixture of tetra-t-butyl α-amino-methylenediphosphonate (5.2 G.) and ethyl thionoformate (8 ml.) contained in a thick-walled, glass tube is cooled to −78° under nitrogen. Hydrogen sulfide (5 ml.) is condensed in the tube which is then sealed. The mixture is brought to room temperature and kept at room temperature overnight. The tube is cooled, opened, and the hydrogen sulfide allowed to evaporate with warming to room temperature. The residue is filtered and the filtrate concentrated in vacuo. The resulting oil is chromatographed on silica gel using 4:1 etheracetone as eluting solvent to afford tetra-t-butyl α-thioformamidomethylenediphosphonate.

By substitution other alcohols for t-butanol in example 2C and by following essentially the procedures of examples 2D and 2E, other α-thioformamido-methylene-diphosphono tetraesters are produced. Examples of alcohols which are used are 2,2,2-trichloroethanol and p-methoxybenzyl alcohol.

Step F: 3-Acetoxy-2-oxo-propyl N-[tetra-t-butyldiphosphonomethyl]-thioformimidate A mixture of tetra-t-butyl α-thioformamidomethylenediphosphonate (1.38 g.), 3-acetoxy-1-chloro-2-propanone (0.47 g.), and anhydrous potassium carbonate (0.44 g.) in acetone (40 ml.) is stirred overnight in a capped flask at room temperature. The mixture is filtered and the salts are washed with acetone. The combined filtrate and washings are evaporated in vacuo, leaving 3-acetoxy-2-oxo-propyl N-[tetra-t-butyldiphosphonomethyl]-thioformimidate.

Step G: Di-t-butyl 5-acetoxymethyl-6H-1,3-thiazine-4-phosphonate

Sodium hydride (0.12 g. of a 57% dispersion in mineral oil, previously washed with petroleum ether) is added to a solution of 3-acetoxy-2-oxo-propyl N-[tetra-t-butyldiphosphonomethyl]-thioformimidate (1.60 g.) in anhydrous dimethoxyethane (50 ml.). The resulting mixture is stirred under nitrogen and heated to 50° for 10 minutes. Benzene (100 ml.) is added to the mixture and the solution is washed with pH9 phosphate buffer, water, and saturated brine. The benzene solution is dried over magnesium sulfate, filtered, and evaporated in vacuo to give crude di-t-butyl 5-acetoxymethyl-6H-1,3-thiazine-4-phosphonate.

Step H: Di-t-butyl d,1-7α-azido-acetoxymethyl-3-cephem-4-phosphonate

The crude thiazine prepared in the previous example is dissolved in anhydrous methylene chloride (50 ml.) and the solution is cooled to −78° under nitrogen. Triethylamine (0.59 ml.) is added with stirring, and then a solution of azidoacetyl chloride (0.37 ml.) in methylene chloride (30 ml.) is added dropwise over 45 minutes. The resulting solution is allowed to warm slowly to room temperature over a period of 3 hours. The solution is washed with several portions of water and saturated brine, dried over magnesium sulfate, filtered, and evaporated in vacuo. The residue is chromatographed on silica gel using 5% acetone in chloroform as eluting solvent to yield di-t-butyl d,1-7α-azido-3-acetoxymethyl-3-cephem-4-phosphonate.

Step I: Di-t-butyl d,1-7α-amino-3-acetoxymethyl-3-cephem-4-phosphonate

A mixture of di-t-butyl d,1-7α-azido-3-acetoxymethyl-3-cephem-4-phosphonate (0.72 g.), platinum oxide (0.30 g.), and dioxane (50 ml.) is hydrogenated at 40 p.s.i. for 2 hours. The mixture is filtered through a parked pad of magnesium sulfate to remove the catalyst. Evaporation of the filtrate in vacuo leaves di-t-butyl d,1-7α-amino-3-acetoxymethyl-3-cephem-4-phosphonate.

Step J: Di-t-butyl d,1-7α-(p-nitrobenzylideneamino)-3-acetoxymethyl-3-cephem-4-phosphonate A mixture of di-t-butyl d,1-7α-amino-3-acetoxymethyl-3-cephem-4-phosphonate (0.42 g.), p-nitrobenzaldehyde (0.14 g.), magnesium sulfate (2.0 g.), and methylene chloride (20 ml.) is stirred overnight at room temperature in a capped flask. The mixture is filtered and the filtrate is evaporated in vacuo to yield di-t-butyl d,1-7α-(p-nitrobenzylideneamino)-3-acetoxymethyl-3-cephem-4-phosphonate.

Step K: Di-t-butyl d,1-7β-(p-nitrobenzylideneamino)-3-acetoxymethyl-3-cephem-4-phosphonate A solution of di-t-butyl d,1-7α-(p-nitrobenzylideneamino)-3-acetoxymethyl-3-cephem-4-phosphonate (0,53 g.) in anhydrous tetrahydrofuran (15 ml.) is cooled to −78° under nitrogen. Phenyllithium (0.41 ml. of a 2.3 N solution) is added rapidly with stirring. Anhydrous dimethylformamide (20 ml.) is then added dropwise over a period of 5 minutes. After having been stirred an additional one minute at −78°, the reaction mixture is quenched with a solution of water (0.17 ml.) and acetic acid (0.13 ml.) in tetrahydrofuran (5 ml.). The mixture is allowed to warm to room temperature. Benzene (200 ml.) is added to the mixture and the resulting solution is washed with water (6×100 ml.). The second wash is acidified with pH3 phosphate buffer and the fifth basified with pH9 phosphate buffer. The benzene solution is dried over magnesium sulfate, filtered, and evaporated in vacuo to afford a mixture of di-t-butyl-7β-(p-nitrobenzylideneamino)-3-acetoxymethyl-3-cephem-4-phosphonate and the corresponding 7α-isomer.

Step L: Di-t-butyl d,1-7β-(and 7α)-amino-3-acetoxymethyl-3-cephem-4-phosphonate 2,4-Dinitrophenylhydrazine (182 mg.) is added to a stirring solution of p-toluenesulfonic acid monohydrate (175 mg.) in ethanol (25 ml.). The mixture is stirred at room temperature for 30 minutes, and then treated with a solution of di-t-butyl d,1-7β and 7α-(p-nitrobenzylideneamino)-3-acetoxymethyl-3-cephem-4-phosphonate (0.53 g.) in chloroform (5 ml.). After stirring for 30 minutes at room temperature, the mixture is filtered and the filtrate is evaporated in vacuo. The residue is partioned between ether (50 ml.) and water (10 ml.) containing 1 M dipotassium hydrogen phosphate (2 ml.). The ethereal phase is dried with magnesium sulfate, filtered, and evaporated in vacuo to afford a mixture of di-t-butyl d,1-7β-amino-3-acetoxymethyl-3-cephem-4-phosphonate and the 7α-amino isomer.

Step M: Di-t-butyl d,1-7β(and α)-(2-thienylacetamido)-3-acetoxymethyl-3-cephem-4-phosphonate.

A mixture of di-t-butyl d,1-7β-amino-3-acetoxymethyl-3-cephem-4-phosphonate and the corresponding 7α-amino isomer (0.37 g.) in anhydrous methylene chloride (10 ml.) is cooled in an ice-bath under nitrogen. Pyridine (0.30 ml.) and a solution of 2-thienylacetyl chloride (0.15 g.) in methylene chloride (1 ml.) are added. The resulting solution is stirred in the cold for 15 minutes. Benzene (50 ml.) is added and the solution is washed with water, pH2 phosphate buffer, water, pH9 phosphate buffer, water, and saturated brine. The organic phase is dried with magnesium sulfate, filtered, and evaporated in vacuo. The residue of di-t-butyl d,1-7β-(2-thienylacetamido)-3-acetoxymethyl-3-cephem-4-phosphonate and di-t-butyl d,1-7β-(2-thienylacetamido)-3-acetoxymethyl-3-cephem-4-phosphonate is separated into the individual isomers by chromatography on silica gel.

Step N: Disodium d,1-7β-(2-thienylacetamido)-3-acetoxymethyl-3-cephem-4-phosphonate Di-t-butyl d,1-7β-(2-thienylacetamido)-3-acetoxymethyl-3-cephem-4-phosphonate (0.14 g.) is dissolved in anhydrous trifluoroacetic acid (3 ml.) and the solution is left at room temperature for 10 minutes. The solvent is removed in vacuo and the residue taken up in water (5 ml.) and brought to pH8.6 with 0.1 N sodium hydroxide. This solution is lyophylized, affording disodium d,1-7β-(2-thienylacetamido)-3-acetoxymethyl-3-cephem-4-phosphonate.

EXAMPLE 3

Disodium d,1-3-acetoxymethyl-7β-(D-2-phenyl-2-hydroxyacetamido)-3-cephem-4-phosphonate

Step A: Disodium d,1-3-acetoxymethyl-7β-amino-3-cephem-4-phosphonate

A solution of dimethyl d,1-3-acetoxymethyl-7β-amino-3-cephem-4-phosphonate (101 mg., 0.3 mmol.) and trimethylchlorosilane (130 mg., 1.2 mmol.) in anhydrous tetrahydrofuran (0.2 ml.) is heated in a sealed tube for 18 hours at 90° C. The tube is opened and the contents evaporated in vacuo to a residue which is stirred for three hours with water (10 ml.). The aqueous mixture is brought to pH8.2 with dilute sodium hydroxide, extracted with chloroform and lyophilized to yield disodium d,1-3-acetoxymethyl-7β-amino-3-cephem-4-phosphonate.

STEP B: Disodium d,1-3-acetoxymethyl-7β-(D-2-phenyl-2-hydroxyacetamido)-3-cephem-4-phosphonate To a solution of 10 mmoles disodium 7β-amino-d,1-3-acetoxymethyl-3-cephem-4-phosphonate in 100 ml. water and 100 ml. acetone containing 5 g NaHCO$_3$ is added 20 mmoles D-phenyl-formyloxyacetyl chloride in 40 ml. acetone at 0° C. After 1 hour stirring at 0° and 2 hours at 25° the acetone is pumped off in vacuo and the aqueous solution added to 100 ml. water and 200 ml. EtOAc. The pH is adjusted to 2.0 with HCl and the ethyl acetate layer dried with MgSO$_4$, filtered and evaporated. The residue is stirred in 50 ml. water containing 2.5 g NaHCO$_3$ and lyophilized, affording the disodium d,1-3-acetoxymethyl-7β-(D-2-phenyl-2-hydroxyacetamido)-3-cephem-4-phosphonate.

EXAMPLE 4

Disodium 7β-(D-α-amino-phenylacetamido)-3-acetoxymethyl-3-cephem-4-phosphonate

Step A: Disodium 7β-(D-α-azido-phenylacetamido)-3-acetoxymethyl-3-cephem-4-phosphonate 1.2 g. of disodium 7β-amino-3-acetoxymethyl-3-cephem-4-phosphonate is dissolved in 5 ml. of acetone and 10 ml. of H$_2$O containing 0.672 g. of sodium bicarbonate. The mixture is cooled to 0° C. and treated with 0.784 g. of D-α-azido-phenyl-acetyl chloride in 5 ml. acetone. The mixture is stirred at 0° C. for 15 minutes and the acetone is removed under reduced pressure. The residual aqueous solution at pH 8 is extracted once with ethyl acetate and then acidified to pH 2 with pH 2 phosphate buffer and extracted with ethyl acetate. The ethyl acetate extract is evaporated and the residue taken up in 50 ml. water containing 0.6 g. NaHCO$_3$ and lyophilized, providing the product, disodium 7β-(D-α-azido-phenylacetamido)-3-acetoxymethyl-3-cephem-4-phosphonate.

Step B: Disodium 7β-(D-α-amino-phenylacetamido)-3-acetoxymethyl-3-cephem-4-phosphonate 0.30 g. of disodium 7β-(D-α-azido)-phenylacetamido-3-acetoxymethyl-3-cephem-4-phosphonate is dissolved in 5 ml. water and 5 ml. dioxane. 0.150 g. of 10% Pd/C catalyst is added, and the mixture reduced under 40 pounds hydrogen pressure for ½ hour. The catalyst is filtered off and the filtrate freeze dried to yield the end product.

EXAMPLE 5

Trisodium 3-acetoxymethyl-7β-(2-carboxy-2-phenylacetamido)-3-cephem-4-phosphonate Step A: 3-Acetoxymethyl-7β-(2-phenyl-2-benzhydryloxycarbonylacetamido)-3-cephem-4-phosphonic acid 2

To a solution of 10 mmoles of disodium 7β-amino-3-acetoxymethyl-3-cephem-4-phosphonate in 100 ml. water and 100 ml. acetone containing 5 g. NaHCO$_3$ is added 20 mmoles of 2-phenyl-2-benzhydryloxycarbonylacetyl chloride in 40 ml. acetone at 0° C. After 1 hour stirring at 0° and 2 hours at 25° the acetone is pumped off in vacuo and the aqueous solution added to 100 ml. water and 200 ml. EtOAc. The pH is adjusted to 2 with HCl and the ethyl acetate layer separated, dried with MgSO$_4$, filtered and evaporated, affording the product, 3-acetoxymethyl-7β-(2-phenyl-21-benzhydryloxycarbonylacetamido)-3-cephem-4-phosphonic acid.

Step B: Trisodium 3-acetoxymethyl-7β-(2-carboxy-2-phenylacetamido)-3-cephem-4-phosphonate One gram of 3-acetoxymethyl-7β-(2-phenyl-2-benzhydryloxycarbonylacetamido)-3-cephem-4-phosphonic acid is dissolved in 2 ml. anisole and treated for two minutes at 0° with 10 ml. trifluoroacetic acid. The mixture is pumped at 0.1 mm at 25° until most of the anisole is removed, and then more anisole is added and pumped off to insure complete removal of TFA. The residue is taken up in 100 ml. water containing three equivalents of NaHCO$_3$, washed with methylene chloride and lyophilized, affording the product, trisodium 3-acetoxymethyl-7β-(2-carboxy-2-phenylacetamido)-3-cephem-4-phosphonate.

EXAMPLE 6

Trisodium 3-acetoxymethyl-7β-(2[3-thienyl]-2-carboxyacetamido)-3-cephem-4-phosphonate Step A: Benzhydryl 3-thienyl malonyl chloride To a slurry of 0.690 g. benzhydryl 3-thienyl malonic acid in 2.5 ml. water is added 2.10 ml. 0.962M NaOH. The solution is filtered and lyophilized, affording the pure sodium salt. This is slurried in 5 ml. benzene and treated at 0° with 1.5 ml. degassed oxalyl chloride. After 10 minutes at 0° and 5 minutes at 25°, the solvent is evaporated and the residue twice dissolved in CCl$_4$ and evaporated. The material is once again taken up in CCl$_4$ and filtered, affording a solution of benzhydryl 3-thienyl malonyl chloride which is evaporated in vacuo, leaving the pure compound.

Step B: 3-Acetoxymethyl-7β-(2-[3-thienyl]-2-benzhydryloxycarbonylacetamido)-3-cephem-4-phosphonic acid To a solution of 10 mmoles disodium 7β-amino-3-acetoxymethyl-3-cephem-4-phosphonate in 100 ml. water and 100 ml. acetone containing 5 g. NaHCO$_3$ is added 20 mmoles benzhydryl 3-thienyl malonyl chloride in 40 ml. acetone at 0° C. After 1 hour stirring at 0° and 2 hours at 25°, the acetone is pumped off in vacuo and the aqueous solution added to 100 ml. water and 200 ml. EtOAc. The pH is adjusted to 2.0 with HCl and the EtOAc layer dried with MgSO$_4$, filtered and evaporated providing 3-acetoxymethyl-7β-(2-[3-thienyl]-2-benzhydryloxycarbonylacetamido)-3-cephem-4-phosphonic acid.

Step C: Trisodium 3-acetoxymethyl-7β-2-[3-thienyl]-2-carboxyacetamido)-3-cephem-4-phosphonate The product of the previous reaction is taken up in 3 ml. anisole and treated with trifluoroacetic acid (12 ml.)

2 minutes at 0°. The mixture is pumped at 25°/0.1 mm. 10 minutes, treated with 3 ml. anisole and pumped again. The residue is taken up in 100 ml. water containing 2.5 g. NaHCO₃, washed with CH₂Cl₂ and lyophilized, providing the title compound.

EXAMPLE 7

Disodium d,
-7β-(2-thienylacetamido)-7α-methoxy-3-acetoxymethyl-3-cephem-4-phosphonate

Step A: Di-t-butyl d,1-7β-(p-nitrobenzylideneamino)-7α-methylthio-3-acetoxymethyl-3-cephem-4-phosphonate A solution of di-t-butyl d,1-7α-(p-nitrobenzylideneamino)-3-acetoxymethyl-3-cephem-4-phosphonate (0.55 g.) in anhydrous tetrahydrofuran (30 ml.) is stirred at −78° under nitrogen. Phenyl lithium (0.44 ml. of a 2.3 M solution) is added via syringe to give the anion. After one more minute, a solution of methylsulfinyl chloride (0.09 g.) in tetrahydrofuran (2 ml.) is added. The resulting solution is allowed to come to room temperature and then diluted with ether (100 ml.) and washed with water (6×50 ml.) and saturated brine. The second wash is acidified with pH 3 phoshate buffer and the fifth basified with pH 9 phosphate buffer. The ethereal solution is dried with magnesium sulfate, filtered and evaporated in vacuo. Chromatography of the residue on silica gel affords di-t-butyl d,1-7β-(p-nitrobenzylideneamino)-7α-methylthio-3-acetoxymethyl-3-cephem-4-phosphonate.

Step B: Di-t-butyl d,1-7β-amino-7α-methylthio-3-acetoxymethyl-3-cephem-4-phosphonate A mixture of 2,4-dinitrophenylhydrazine (91 mg.) and p-toluenesulfonic acid monohydrate (88 mg.) in tetrahydrofuran (2 ml.) is stirred at room temperature for 30 minutes. The resulting suspension is treated with a solution of di-t-butyl d,1-7β-(p-nitrobenzylideneamino)-7α-methylthio-3-acetoxymethyl-3-cephem-4-phosphonate (304 mg.) in tetrahydrofuran (2 ml.). After stirring for 1 hour at room temperature, the reaction mixture is filtered and the filtrate is evaporated in vacuo. The residue is dissolved in methylene chloride and the solution washed with pH 9 phosphate buffer, water and saturated brine. The organic portion is dried with magnesium sulfate, filtered and evaporated in vacuo, yielding di-t-butyl d,1-7β-amino-7α-methylthio-3-acetoxymethyl-3-cephem-4-phosphonate.

Step C: Di-t-butyl d,1-7β-(2-thienylacetamido)-7α-methylthio-3-acetoxymethyl-3-cephem-4-phosphonate A solution of di-t-butyl d,1-7β-amino-7α-methylthio-3-acetoxymethyl-3-cephem-4-phosphonate (185 mg.) in dry methylene chloride (5 ml.) is cooled to 5° under nitrogen. Pyridine (100 ml.) and a solution of 2-thienylacetyl chloride (65 mg.) in methylene chloride (1 ml.) are added. The resulting solution is stirred in the cold for 15 minutes. Benzene (50 ml.) is added and the solution is washed with water (5×25 ml.) and saturated brine (25 ml.). The second was acidified with pH 2 phosphate buffer and the fourth basified with pH 9.2 phosphate buffer. The benzene solution is dried with magnesium sulfate, filtered and evaporated in vacuo to an oil. This material is chromatographed on a column of silica gel to afford di-t-butyl d,1-7β-(2-thienylacetamido)-7α-methylthio-3-acetoxymethyl-3-cephem-4-phosphonate.

Step D: Di-t-butyl d,17β-(2-thienylacetamido-7α-methoxy-3-acetoxymethyl-3-cephem-4-phosphonate To a solution of di-t-butyl d,1-7β-(2-thienylacetamido)-7α-methylthio-3-acetoxymethyl-3-cephem-4-phosphonate (188 mg.) in methanol (4 ml.) is added a solution of thallium trinitrate trihydrate (147 mg.) in methanol (2 ml.). The resulting mixture is stirred at room temperature for 10 minutes. Sodium bicarbonate (84 mg.) is then added and stirring is continued for two more minutes. The mixture is filtered and the filtrate is evaporated in vacuo to dryness. The residue is taken up in methylene chloride and filtered. The filtrate is washed with water, pH 9 phosphate buffer, water and saturated brine, dried with magnesium sulfate, filtered and evaporated in vacuo to an oil. Chromatography of this material on a silica gel column yields di-t-butyl d,1-7β-(2-thienylacetamido)-7α-methoxy-3-acetoxymethyl-3-cephem-4-phosphonate.

Step E: Disodium d,1-7β-(2-thienylacetamido-7α-methoxy-3-acetoxymethyl-3-cephem-4-phosphonate A solution of di-t-butyl d,1-7β-(2-thienylacetamido)-7α-methoxy-3-acetoxymethyl-3-cephem-4-phosphonate (106 mg.) in anhydrous trifluoro acetic acid (10 ml.) is stirred at room temperature for 10 minutes. The solvent is then evaporated in vacuo and the residue taken up in water and adjusted to pH 8.5 with 0.1N sodium hydroxide. The aqueous solution is washed with ethyl acetate, pumped under vacuum to remove dissolved ethyl acetate and lyophylized to give disodium d,1-7β-(2-thienylacetamido)-7α-methoxy-3-acetoxymethyl-3-cephem-4-phosphonate as an amorphous powder.

EXAMPLE 8

Dimethyl
d,1-3-acetoxymethyl-7β-(2′-thienylacetamido)-7-methoxy-3-cephem-4-phosphonate

Step A: Dimethyl d,1-3-acetoxymethyl-7β-(p-nitrobenzylideneamino)-7-bromo-3-cephem-4-phosphonate Dimethyl d,1-3-acetoxymethyl-7β-(p-nitrobenzylideneamino)-3-cephem-4-phosphonate (527 mg.) is dissolved in 20 ml. of dry tetrahydrofuran. At −78° C., under nitrogen, 0.435 ml. of 2.3 M phenyl lithium is added. The reaction mixture is stirred at −78° C. for 5 minutes. 0.2 Grams of N-bromosuccinimide in 3 ml. of anhydrous tetrahydrofuran is then added. The cooling bath is removed and the reaction mixture allowed to come to 0° C. The solvent is removed under reduced pressure and the residue taken up in methylene chloride (30 ml.) and washed with pH 7 phosphate buffer and then with water, dried, and evaporated to a volume of about 12 ml. This solution of dimethyl d,1-3-acetoxymethyl-7β-(p-nitrobenzylideneamino)-7-bromo-3-cephem-4-phosphonate is used directly in the next step.

Step B: Dimethyl d,1-3-acetoxymethyl-7β-(p-nitrobenzylideneamino)-7-methoxy-3-cephem-4-phosphonate Silver oxide (0.2 g.) is suspended in 20 ml. of methanol. The solution of the 7-bromo derivative obtained in Step A is added dropwise over 10 minutes to the silver oxide suspension. The reaction mixture is stirred for another 15 minutes. The silver salts are removed by filtration, the filtrate evaporated and the residue taken up in benzene and washed twice with pH 7 phosphate buffer, then dried and evaporated to afford dimethyl d,1-3-acetoxymethyl-7β-(p-nitrobenzylideneamino)-7-methoxy-3-cephem-4-phosphonate.

Step C: Dimethyl d,1-3-acetoxymethyl-7β-(2'-thienylacetamido)-7-methoxy-3-cephem-4-phosphonate 50 mg. of dimethyl d,1-3-acetoxymethyl-7β-(p-nitrobenzylideneamino)-7-methoxy-3-cephem-4-phosphonate is dissolved in 4 ml. of methylene chloride, cooled to 0° C. and 0.08 ml. of thienylacetyl chloride added. To this is added 0.4 ml. of a 1% solution of water in tetrahydrofuran and the mixture stirred at 0° C. for two minutes. 0.2 ml. of pyridine is then added dropwise over 30 minutes. The reaction mixture is then washed with pH 2 phosphate buffer followed by pH 7 buffer, then dried and evaporated to yield the desired product, after purification using preparative TLC on silica gel using 2% methanol/chloroform as eluant, to afford dimethyl d,1-3-acetoxymethyl-7β-(2'-thienylacetamido)-7-methoxy-3-cephem-4-phosphonate.

EXAMPLE 9

Dimethyl d,1-3-acetoxymethyl-7β-phenylacetamido-7-methoxy-3-cephem-4-phosphonate Dimethyl d,1-3-acetoxymethyl-7β-(p-nitrobenzylideneamino)-3-cephem-4-phosphonate (0.14 g.) is dissolved in 6 ml. tetrahydrofuran, 1 ml. of water is added and then 0.025 g. of PdCl$_2$. The mixture is stirred at room temperature for 3 hours. The solvent is removed under reduced pressure at ambient temperature. The residue is triturated with petroleum ether and the soluble material is discarded. The residue is taken up in 25 ml. methylene chloride, dried over MgSO$_4$ and evaporated to afford the residue containing the 7-amino complex which is taken up in 4 ml. of methylene chloride, cooled to 0° C., treated with 0.142 g. of pyridine and then with 0.042 ml. of phenylacetylchloride. The reaction mixture is stirred at 0° C. for 15 minutes. The reaction mixture is diluted with methylene chloride and washed once with pH 2 buffer and then with pH 7 buffer. The organic phase is dried and evaporated to afford the crude product which is purified by thin layer chromatography to afford dimethyl d,1-3-acetoxymethyl-7β-phenylacetamido-7-methoxy-3-cephem-4-phosphonate.

EXAMPLE 10

Disodium d,1-7β-(2-thienylacetamido)-3-methyl-3-cephem-4-phosphonate

Step A: 2-Oxo-propyl N-tetramethyldiphosphonomethyl-thioformimidate

Anhydrous powdered potassium carbonate (0.95 g.) is added to a solution of tetramethyl α-thioformamidomethylenediphosphonate (2.00 g.) in acetone (90 ml.). The mixture is stirred under nitrogen for 5 minutes and then it is treated with a solution of 1-chloro-2-propanone (0.63 g.) in acetone (10 ml.). The resulting mixture is stirred overnight at room temperature. The salts are filtered off and the filtrate is evaporated in vacuo. The residue is 3 times taken up in benzene and evaporated in vacuo to afford 2-oxo-propyl N-tetramethyldiphosphonomethyl-thioformimidate (2.20 g.): nmr (CDCl$_3$) δ2.32 (S, 3, CH$_3$), 3.84 (M, 14, OCH$_3$ and SCH$_2$), 4.39 (t, 1, J=19H$_Z$, CH) and 8.40 (t, 1, J=3H$_Z$, N=CH).

Step B: Dimethyl 5-methyl-6H-1,3-thiazine-4-phosphonate

Sodium hydride (0.39 g. of a 57% dispersion in mineral oil, washed with petroleum ether) is added to a solution of 2-oxo-propyl N-tetramethyldiphosphonomethylthioformimidate (2.20 g.) in anhydrous dimethoxyethane (20 ml.). The mixture is stirred under nitrogen for 10 minutes at 50° (oil bath) and then diluted with benzene (40 ml.). The solution is washed with pH 7 phosphate buffer, water and saturated brine, dried with magnesium sulfate, filtered and evaporated in vacuo to afford dimethyl 5-methyl-6H-1,3-thiazine-4-phosphonate (0.87 g.):
nmr (CDCl$_3$) λ 2.36 (d, 3, J=3H$_Z$, CH$_3$), 3.28 (M, 2, SCH$_2$), 3.79 (d, 6, J=12H$_Z$, OCH$_3$) and 8.28 (S, 1, N=CH).

Step C: Dimethyl d,1-7β-azido-3-methyl-3-cephem-4-phosphonate

A solution of dimethyl 5-methyl-6H-1,3-thiazine-4-phosphonate (0.87 g.) in anhydrous methylene chloride (40 ml.) is cooled to −78° under nitrogen. Triethylamine (0.60 ml.) is added and then a solution of azidoacetyl chloride (0.39 ml.) in methylene chloride (20 ml.) is added dropwise over 30 minutes. The resulting solution is allowed to warm slowly to room temperature over a period of 3 hours. The solution is washed 4 times with water and saturated brine, dried with magnesium sulfate, filtered and evaporated to an oil (1.21 g.). This material is combined with crude product (0.37 g.), obtained from another run and chromatographed on silica gel (40 g.). Elution with 5% acetone in chloroform affords dimethyl d,1-7α-azido-3-methyl-3-cephem-4-phosphonate (0.70 g.): ir (CHCl$_3$) 4.72, 5.60, 7.51, 8.0, 9.65 and 11.92 μ:nmr (CDCl$_3$) δ2.31 (d, 3, J=3H$_Z$, CH$_3$), 3.21 (splintered S, 2, SCH$_2$), 3.80 and 3.83 (two doublets, 6, J=11H$_Z$, OCH$_3$), and 4.56 (S, 2, H6 and H7).

Step D: Dimethyl d,1-7α-amino-3-methyl-3-cephem-4-phosphonate

Hydrogen sulfide is bubbled into an ice-cold solution of dimethyl d,1-7α-azido-3-methyl-3-cephem-4-phosphonate (0.31 g.) and triethylamine (0.6 ml.) in chloroform (14 ml.). After 6 minutes an ir spectrum shows absence of azido absorption and the hydrogen sulfide flow is stopped. The solution is brought to room temperature and evaporated under reduced pressure. The residue is dissolved in chloroform and the solution is washed with three portions of water and saturated brine. The aqueous portion is backwashed with more chloroform. The combined organic solution is dried with magnesium sulfate, filtered and concentrated in vacuo, affording dimethyl d,1-7α-amino-3-methyl-3-cephem-4-phosphonate (0.31 g.): ir (CHCl$_3$) 5.64μ; nmr (CDCl$_3$)δ2.26 (d, 3, J=3H$_Z$, CH$_3$), 3.18 (splintered S, 2, SCH$_2$), 3.80 and 3.86 (two doublets, 6, J=11H$_Z$, OCH$_3$), 4.16 (d, 1, J=2H$_Z$, H6 or H7) and 4.48 (d, 1, J=2H$_Z$, H7 or H6).

Step E: Dimethyl d,1-7α-(p-nitrobenzylideneamino)-3-methyl-3-cephem-4-phosphonate A mixture of dimethyl d,1-7α-amino-3-methyl-3-cephem-4-phosphonate (0.31 g.), p-nitrobenzaldehyde (0.13 g.) and magnesium sulfate (1.6 g.) in methylene chloride (20 ml.) is stirred at room temperature and under nitrogen for 18 hours. The mixture is filtered and the filtrate evaporated in vacuo. Trituration of the residue with diethyl ether yields crystalline dimethyl d,1-7α-(p-nitrobenzylideneamino)-3-methyl-3-cephem-4-phosphonate (0.17 g.): ir (CH$_2$Cl$_2$) 5.61, 6.10, 6.24 and 9.7μ; nmr (CDCl$_3$)δ 2.36 (d, 3, J=3H$_Z$, CH$_3$), 3.35 (S, 2, SCH$_2$), 3.84 and 3.90 (two doublets, 6, J=12H$_Z$, OCH$_3$), 4.87 (d, 1, J=1.5 H$_Z$, H6 or H7), 4.94 (d, 1, J=1.5 H$_Z$, H7 or H6), 7.99 and 8.32 (two doublets, 4, J=9H$_Z$, ArH), and 8.61 (S, 1, CH=N).

Step F: Dimethyl d,1-7β-(p-nitrobenzylideneamino)-3-methyl-3-cephem-4-phosphonate A solution of dimethyl d,1-7α-(p-nitrobenzylideneamino)-3-methyl-3-cephem-4-phosphonate (0.19 g.) in anhydrous tetrahydrofuran (6 ml.) is cooled to −78° under nitrogen. Phenyl lithium (0.2 ml. of a 2.3M solution) is added with stirring. Anhydrous dimethylformamide (8.9 ml.) is then added dropwise over 4 minutes. After stirring an additional 1.5 minutes at −78°, the reaction mixture is quenched by addition of a solution of water (83 ml.) and acetic acid (66 ml.) in tetrahydrofuran (6.5 ml.). The mixture is allowed to warm to room temperature. Benzene (100 ml.) is added and the solution is washed with water (6×40 ml.). The second wash is acidified with pH 3 phosphate buffer (0.5 ml. of a 1M solution) and the fifth is basified with pH 9 phosphate buffer (0.5 ml. of a 1M solution). The benzene solution is dried with magnesium sulfate, filtered and evaporated in vacuo to yield a mixture of dimethyl d,1-7α-(p-nitrobenzylideneamino)-3-methyl-3-cephem-4-phosphonate and dimethyl d-1-7β-(p-nitrobenzylideneamino)-3-methyl-3-cephem-4-phosphonate.

Step G: Dimethyl d,1-7β(and α)-amino-3-methyl-3-cephem-4-phosphonate 2,4-Dinitrophenylhydrazine (91 mg.) is added to a solution of p-toluenesulfonic acid monohydrate (87 mg.) in ethanol (10 ml.). The resulting mixture is stirred at room temperature for 45 minutes, then treated with a solution of the schiff base mixture obtained by the previous example in chloroform (2 ml.). The mixture is stirred at room temperature for 30 minutes, filtered and the filtrate is evaporated in vacuo. The residue is taken up in chloroform and filtered. The filtrate is washed with pH 9 phosphate buffer and saturated sodium chloride, dried over magnesium sulfate, filtered and evaporated in vacuo. The residue (58 mg.) is a mixture of dimethyl d,1-7α-amino-3-methyl-3-cephem-4-phosphonate and dimethyl d,1-7β-amino-3-methyl-3-cephem-4-phosphonate.

Step H: Dimethyl d,1-7β(and α)-(2-thienylacetamido)-3-methyl-3-cephem-4-phosphonate The amine mixture (58 mg.) obtained in the previous example is dissolved in dry methylene chloride (5 ml.) and the solution is cooled in an ice-bath. Pyridine (116 ml.) and a solution of 2-thienylacetyl chloride (106 mg.) in dry methylene chloride (2 ml.) are added. The resulting solution is stirred in the cold for 30 minutes. More solvent is added and the solution is washed with pH 2 phosphate buffer, water, pH9 phosphate buffer, H$_2$O and saturated brine, dried over magnesium sulfate, filtered and evaporated in vacuo. The crude residue (137 mg.) of dimethyl d,1-7α-(2-thienylacetamido)-3-methyl-3-cephem-4-phosphonate and dimethyl d,1-7β-(2-thienylacetamido)-3-methyl-3-cephem-4-phosphonate is purified by preparative silica gel layer chromatography using 5% methanol in chloroform as developing solvent. The product band affords dimethyl d,1-7β-(2-thienylacetamido)-3-methyl-3-cephem-4-phosphonate (19 mg.): ir (CHCl$_3$) 5.64, 5.98 and 9.62μ; nmr (CDCl$_3$) δ 2.22 (d, 3, J=3H$_Z$, CH$_3$), 3.06 and 3.30 (AB$_9$, 2, J=18H$_Z$, SCH$_2$), 3.80 (M, 8, OCH$_3$ and thienyl-CH$_2$), 4.89 (d, 1, J=4H$_Z$, H6), 5.60 (d cf d, 1, J=8 H$_Z$ and J=4 H$_Z$, H7), 6.52 (d, 1, J=8H$_Z$, NH), 6.95 (M, 2, ArH) and 7.20 (M, 1, ArH).

Step I: Sodium methyl d,1-7β-(2-thienylacetamide)-3-methyl-3-cephem-4-phosphonate Dimethyl d,1-7β-(2-thienylacetamido)-3-methyl-3-cephem-4-phosphonate (10 mg.) is dissolved in an ice-cold mixture of pyridine (0.36 ml.) and water (0.54 ml.). Sodium hydroxide (0.24 ml. of a 0.1N solution) is added and the resulting solution is stirred in the cold for 3 hours. The solution is evaporated in vacuo to dryness. The residue is taken up in water and the solution acidified to pH 7.8 with dilute hydrochloric acid. The solution is extracted with 3 portions of chloroform to remove any starting material. The aqueous phase is lyophilized to afford crude sodium methyl d,1-7β-(2-thienylacetamido)-3-methyl-3-cephem-4-phosphonate (10 mg.) as an amorphous, off-white powder.

Step J: Disodium d,1-7β-2-thienylacetamido)-3-methyl-3-cephem-4-phosphonate

A solution of sodium methyl d,1-7β-(2-thienylacetamido)-3-methyl-3-cephem-4-phosphonate (8 mg.) in water (0.5 ml.) is acidified to pH 2 with dilute hydrochloric acid. The solution is left at room temperature for 3 hours. The pH is brought to 8.6 with dilute sodium hydroxide and the solution is lyophilized, affording disodium d,1-7β-(2-thienylacetamido)-3-methyl-3-cephem-4-phosphonate (9 mg.).

EXAMPLE 11 d,1-7β-(D-α-aminophenylacetamido)-3-methyl-3-cephem-4-phosphonic acid, mono sodium salt

Step A: Dimethyl d,1-7β(and α)-(D-α-azidophenylacetamido)-3-methyl-3-cephem-4-phosphonate To an ice-cold stirring solution of dimethyl d,1-7β(and α)-amino-3-methyl-3-cephem-4-phosphonate (0.28 g.) as prepared in Example 10, Step G, in dry methylene chloride (5 ml.) is added successively pyridine (0.3 ml.) and D-α-azido-phenylacetyl chloride (0.20 g.). The resulting solution is stirred in the cold for 15 minutes. More methylene chloride is added and the solution is washed with water, pH 2 phosphate buffer, water, pH 9 phosphate buffer, water and saturated brine. The organic phase is dried with magnesium sulfate, filtered and evaporated in vacuo to dryness. The residue is chromatographed on silica gel using 5% methanol in chloroform as eluting solvent to afford dimethyl d,l-7β-(D-α-azido-phenylacetamido)-3-methyl-3-cephem-4-phosphonate and the corresponding 7α-isomer.

Step B: Dimethyl d,1-7β-(D-α-amino-phenylacetamido)-3-methyl-3-cephem-4-phosphonate A mixture of dimethyl d,l-7β-(D-α-azido-phenylacetamido)-3-methyl-3-cephem-4-phosphonate (0.16 g.), 10% palladium on carbon (0.05 g.) and methanol (10 ml.) is hydrogenated at 40 p.s.i. for 2 hours. The mixture is filtered through a pad of diatomaceous earth which is washed with more methanol. The filtrate and washings are evaporated in vacuo to dryness, yielding dimethyl d,l-7β-(d-α-amino-phenylacetamido)-3-methyl-3-cephem-4phosphonate.

Step C: d,-17β-(D-α-amino-phenylacetamido)-3-methyl-3-cephem-4-phosphonic acid, mono sodium salt Dimethyl d,l-7β-(D-α-amino-phenylacetamido)-3-methyl-3-cephem-4-phosphonate (0.10 g.) is dissolved in an ice-cold mixture of pyridine (3 ml.) and water (3 ml.). Sodium hydroxide (2.4 ml. of a 0.1N solution) is added and the resulting solution is stirred in the cold for 2 hours. The solution is evaporated in vacuo to dryness. The residue is taken up in water (5 ml.) and extracted with chloroform. The aqueous portion is separated and acidified to pH 2 with 1N hydrochloric acid. After standing for 3 hours at room temperature, the mixture is basified to pH 8.5 with dilute sodium hydroxide, cooled in ice and diluted to cloudiness with acetone. The precipitate of crude d,l-7β-(D-α-amino-phenylacetamido)-3-methyl-3-cephem-4-phosphonic acid mono sodium salt is collected and dried under vacuum.

EXAMPLE 12

Disodium d,l-3-pyridinium-methyl-7β-(2'-thienylacetamido)-3-cephem-4-phosphonate A solution of disodium d,l-3-acetoxymethyl-7β-(2'-thienylacetamido)-3-cephem-4-phosphonate (1.0 g.) is brought to pH 2.5. Pyridine (8.0 ml.) is added and the solution is allowed to stnd overnight at 45° C. The reaction mixture is then lypholized and the residue is dissolved in water and passed through a polystyrene trimethylbenzylammonium anion exchange resin (43% H₂O). Selected fractions are diluted with water and lyophilized to afford substantially pure disodium d,l-3-pyridinium-methyl-7β-(2'-thienylacetamido)-3-cephem-4-phosphonate.

EXAMPLE 13

Disodium 3-(5-methyl-1,3,4-thiadiazole-2-ylthiomethyl)-7β-(2'-thienylacetamido-3-cephem-4-phosphonate and Disodium 7β-(2'-thienylacetamido)-3-(N-methyltetrazolythiomethyl)-3-cephem-4-phosphonate A mixture of dimethyl d,l-3-acetoxymethyl-7β-(2'-thienylacetamido)-3-cephem-4-phosphonate (0.65 g.) and 5-methyl-1,3,4-thiadiazolyl-2-thiol (0.37 ml.) in a mixture of one part acetone and one part water (10 ml.) is stirred at room temperature and a 10% sodium hydroxide solution (2.0 ml.) is added with stirring. The mixture is then heated in a sealed tube for 100 hours and the resulting mixture is concentrated in vacuo to afford disodium 3-(5-methyl-1,3,4-thiadiazole-2-ylthiomethyl)-7β-(2'-thienylacetamido)-3-cephem-4-phosphonate.

By substituting for the 5-methyl-1,3,4-thiadiazolyl-2-thiol an equimolar quantity of N-methyltetrazolylthiol and by following substantially the procedure described above, there is obtained disodium d,l-3-(N-methyltetrazolylthiometyl)-7β-(2'-thionylacetamido-3-cephem-4-phosphonate.

EXAMPLE 14

Disodium 7β-amino-3-(2-methyl-1,3,4-thiadiazolyl-5-thiomethyl)-3-cephem-4-phosphonate and Disodium 7β-amino-3-(1-methyl-1,2,3,4-tetrazolyl-5-thiomethyl)-3-cephem-4-phosphonate To a mixture of 1 g. disodium 7β-amino-3-acetoxymethyl-3-cephem-4-phosphonate, 10 ml. water and 5 ml. acetone, is added NaHCO₃ until the pH of the solution is 7.9. A solution of 1½ equivalents 2-methyl-1,3,4-thiadiazole-5-thiol in 10 ml. acetone is added and the reaction kept in an 80° C. water bath for 3 hours. The mixture is then evaporated in vacuo, taken up in water and lyophilized, affording the title compound, disodium 7β-amino-3-(2-methyl-1,3,4-thiadiazolyl-5-thiomethyl)-3-cephem-4-phosphonate.

To prepare the second compound, the reactant 1-methyl-1,2,3,4-tetrazolo-5-thiol is used in place of 2-methyl-1,3,4-thiadiazole-5-thiol.

EXAMPLE 15

Disodium 7β-(D-2-phenyl-2-hydroxyacetamido)-3-(1,methyl-1,2,3,4-tetrazolyl-5-thiomethyl)-3-cephem-4-phosphonate (Compound I)

and

Disodium 7β-(D-2-phenyl-2-hydroxyacetamido)-3-(2-methyl-1,3,4-thiadiazolyl)-3-cephem-4-phosphonate (Compound II)

To a solution of 10 mmoles disodium 7β-amino-3-(1-methyl-1,2,3,4-tetrazolyl-5-thiomethyl)-3-cephem-4-phosphonate in 100 ml. water and 100 ml. acetone containing 5 g. NaHCO₃ is added 20 mmoles of D-phenylformyloxyacetyl chloride in 40 ml. acetone of 0° C. After 1 hour stirring at 0° and 2 hours at 25°, the acetone is pumped off in vacuo and the aqueous solution added to 100 ml. water and 200 ml. EtOAc. The pH is adjusted to 2.0 with HCl and the ethyl acetate layer dried with MgSO₄, filtered and evaporated. The residue is stirred in 50 ml. water containing 2.5 g. NaHCO₃ and lyophilized, affording the title copound I.

When the above reaction is done using as staring material disodium 7β-amino-3-(2-methyl-1,3,4-thiadiazolyl-5-thiomethyl)-3-cephem-4-phosphonate, the title compound II is obtained.

EXAMPLE 16

Disodium
7β-(2-tetrazolylacetamido)-3-(2-methyl-1,3,4-thiadiazolyl-5-thiomethyl)-3-cephem-4-phosphonate To a solution of 10mmoles 7β-amino-3-(2-methyl-1,3,4-thiadiazolyl-5-thiomethyl)-3-cephem-4-phosphonate in 100 ml. water and 100 ml. acetone containing 5 g $NaHCO_3$ is added 20 mmoles 2-tetrazolacetyl chloride in 40 ml acetone at 0° C. After 1 hr. stirring at 0° and 2 hrs at 25° the acetone is pumped off in vacuo and the aqueous solution added to 100 ml. water and 200 ml EtOAc. The pH is adjusted to 2 with HCl and the ethyl acetate layer separated and evaporated.

The redidue is taken up in 50 ml. water containing 1.6 g. $NaHCO_3$ and lyophilized, providing the title compound.

EXAMPLE 17

Disodium
7β-(2-furylacetamido)-3-(N-methyltetrazolylthiomethyl)-3-cephem-4-phosphonate To a solution of 10 mmoles 7β-amino-3-(N-methyltetrazolylthiomethyl)-3-cephem-4-phosphonate in 100 ml. water and 100 ml. acetone containing 5 g. $NaHCO_3$ is added 20 mmoles 2-furylacetyl chloride in 40 ml acetone at 0° C. After 1 hr. stirring at 0° and 2 hrs at 25° the acetone is pumped off in vacuo and the aqueous solution added to 100 ml. water and 200 ml. EtOAc. The pH is adjusted to 2 with HCl and the ethyl acetate layer separated, and evaporated. The residue is taken up in 50 ml water containing 1.6 g. $NaHCO_3$ and lyophilized, providing the title compound.

EXAMPLE 18

Disodium
7β-(D-α-amino)-phenylacetamido-3-carbamoyloxymethyl-3-cephem-4-phosphonate Step A: Disodium 7β-(D-α-azido-phenylacetamido)-3-hydroxymethyl-3-cephem-4-phosphonate Disodium 7β-(D-α-azido-phenylacetamido)-3-acetoxymethyl-3-cephem-4-phosphonate 1 g.) is dissolved in 100 ml. of a solution of citrus acetyl esterase (J. D. A. Jeffery, et. al., Biochem. J. (1961) 81, 591). The pH is adjusted to 6.6 and the mixture is maintained at 30° C. 1 N NaOH is added dropwise to maintain the pH at 6.6 as the reaction proceeds and the reaction is continued until no further pH change occurs. 10 g. NaCl is added and the mixture is layered with 50 ml. EtOAc, the pH is adjusted to 2.1 with HCl and the mixture is stirred vigorously. The EtOAc layer is separated and washed once with water and then layered with water and stirred and the pH of the aqueous phase is adjusted to 5.9 with 6 N NaOH. The aqueous layer is separated and freeze-dried to give the title compound.

Step B: Disodium
7-β-(D-α-azido-phenylacetamido)-3-carbamoyloxymethyl-3-cephem-4-phosphonate 0.50 g. of the disodium 7-β-(D-α-azido-phenylacetamido)-3-hydroxymethyl-3-cephem-4-phosphonate is dissolved in 10 ml. of 0.05 M $NaH_2PO_4$ and the pH is adjusted to 2.2 with 2.5 N HCl. The mixture is extracted with ethyl acetate 3 times and the combined ethyl acetate extract is dried and evaporated to 2 ml. This is diluted with 20 ml. THF and cooled to −78° C. and treated with 0.141 g. of chlorosulfonylisocyanate. The reaction mixture is stirred for 1½ hours at −78° C. then treated with 0.1 M pH 2 phosphate buffer (2 ml.) and the THF is removed under reduced pressure. Ethylacetate (10 ml.) and 0.1 M pH 2 phosphate buffer (10 ml.) are added and the mixture is stirred for 1 hour at room temperature. The pH of the aqueous layer is adjusted to 8, the mixture shaken and the organic phase is separated. The aqueous phase is adjusted to pH 2 and extracted with ethyl acetate. 3×30 ml. The ethyl acetate extracted is evaporated and the residue taken up in 25 ml. water containing 0.3 g. $NaHCO_3$ and lyophilized, affording the title compound.

Step C: Disodium
7β-(D-α-amino-phenylacetamido)-3-carbamoyloxymethyl-3-cephem-4-phosphonate 0.30 g. of disodium 7β-(Dα-azido-phenylacetamido)-3-carbamoyloxymethyl-3-cephem-4-phosphonate is dissolved in 5 ml. $H_2O$ and 5 ml. dioxane, 0.150 g. of 10% Pd/C (Bolhofer catalyst) is added and the mixture is reduced under 40 lbs $H_2$ pressure for ½ hour. The catalyst is filtered off and the filtrate is freeze-dried to give the title compound.

If the product from Step A, disodium 7β-(D-α-azido-phenylacetamido)-3-hydroxymethyl-3-cephem-4-phosphonate, is created with catalytic hydrogen as is Step C, the product, disodium 7β-(D-α-amino-phenylacetamido)-3-hydroxymethyl-3-cephem-4-phosphonate results.

EXAMPLE 19

Trisodium
3-hydroxymethyl-7β-(2-[3-thienyl]-2-carboxyacetamido)-3-cephem-4-phosphonate Trisodium 3-acetoxymethyl-7β-(2-[3-thienyl]-2-carboxyacetamido)-3-cephem-4-phosphonate (1 g.) is dissolved in 100 ml. of a solution of citrus acetyl esterase (J. D. A. Jeffery, et. al., Biochem. J. (1961) 81, 591). The pH is adjusted to 6.6 and the mixture is maintained at 30° C. 1 N NaOH is added dropwise to maintain the pH at 6.6 as the reaction proceeds and the reaction is continued until no further pH change occurs. 10 g. NaCl is added and the mixture is layered with 50 ml. EtOAc, the pH is adjusted to 2.1 with HCl and the mixture is stirred vigorously. The EtOAc layer is separated and washed once with water and then layered with water and stirred and the pH of the aqueous phase is adjusted to 5.9 with 6 N NaOH. The aqueous layer is separated and freeze-dried to give trisodium 3-hydroxymethyl-7β-(2-[3-thienyl]-2-carboxyacetamido)-3-cephem-4-phosphonate.

EXAMPLE 20

Trisodium
3-carbamoyloxymethyl-7β-(2-[1½-thienyl]-2-carboxyacetamido)-3-cephem-4-phosphonate 0.5 g. of the trisodium 3-hydroxymethyl-7β-(2-[3-thienyl]-2-carboxyacetamido)-3-cephem-4-phosphonate is dissolved in 10 ml. of 0.05 M $NaH_2PO_4$ and the pH is adjusted to 2.2 with 2.5 N HCl. The mixture is extracted with ethyl acetate 3 times and the combined ethyl acetate extract is dried and evaporated to 2 ml. This is diluted with 20 ml. THF and cooled to −78° C. and treated with 0.141 g. of chlorosulfonylisocyanate. The reaction mixture is stirred for 1½ hours at −78° C. then treated with 0.1 M pH 2 phosphate buffer (2 ml.) and the THF is removed under reduced pressure. Ethylacetate (10ml.) and 0.1 M pH 2 phosphate buffer (10 ml.) are added and the mixture is stirred for 1 hour at room temperature. The pH of the aqueous layer is adjusted to 8, the mixture shaken and the organic phase is separated. The aqueous phase is adjusted to pH 2 and extracted with ethyl acetate. $3 \times 30$ ml. The ethyl acetate extract is dried, evaporated, dissolved in water and the pH adjusted to 5.9. Freeze-drying affords trisodium 3carbamoyloxymethyl-7$\beta$-(2-[3-thienyl]-2-carboxyacetamido)-3-cephem-4-phosphonate.

EXAMPLE 21

Sodium d,l-3-acetoxymethyl 7$\beta$-(2-thienylacetamido)-3-cephem-4-sulfonate

Step A: Diethyl benzalimino(p-nitrophenoxysulfonyl)methyl phosphonate

Diethyl benzaliminomethyl phosphonate (25.5 g) is dissolved in 300 ml THF, cooled to $-78°$ C. and 100 ml of 1 M phenyl lithium in $Et_2O/C_6H_6$ is added dropwise over 10 min. The solution is stirred for 15 min and treated with 21 g of p-nitrophenyl chlorosulfate in 100 ml THF added as rapidly is possible. The reaction mixture is stirred at $-78°$ for a further 15 minutes and allowed to warm to room temperature. The THF is removed under reduced pressure and the residue is taken up in $CH_2Cl_2$ (300 ml) and washed once with pH 3 phosphate buffer and then with brine. The organic phase is dried and evaporated to give crude product which is purified by chromatography on silica gel to give diethyl benzalimino-(p-nitrophenoxysulfonyl)-methyl phosphonate.

Step B: p-Toluene sulfonic acid salt diethyl amino(p-nitrophenyloxysulfonyl)-methyl phosphonate 21.25 g of diethyl benzalimino-(p-nitrophenyloxysulfonyl)methyl phosphonate is dissolved in 200 ml $Et_2O$ and added over 15 min to a solution of 9.5 g of p-toluene sulfonic acid monohydrate in 150 ml $Et_2O$. 60 ml. of cyclohexane is then added and the mixture allowed to settle. The supernatant solvent is decanted and the residual oil is washed twice with a mixture of 2:1 ether cyclohexane. The residual oil is the p-toluene sulfonic acid salt of diethyl amino-(p-nitrophenyloxysulfonyl)-methyl phosphonate.

Step C: Diethylamino(p-nitrophenylsulfonyl)methyl phosphonate 25 g of the p-toluene sulfonic acid salt of diethyl amino(p-nitrophenyloxysulfonyl)methyl phosphonate is partitioned between $CH_2Cl_2$ and 30 ml. of 1 M $K_2HPO_4$ and the organic phase is separated. The aqueous phase is extracted three times with $CH_2Cl_2$ and the combined organic extract is dried and evaporated to give diethyl amino(p-nitrophenylsulfonyl)-methylphosphonate.

Step D: Diethyl thioformamido-(p-nitrophenylsulfonyl) methyl phosphonate 12.2 g. of diethyl amino-(p-nitrophenyloxysulfonyl)-methylphosphonate is placed in a pressure tube. 4 g. of ethyl thionoformate is added and then 4 ml of $H_2S$ is condensed into the tube at $-78°$. The tube is sealed, the contents are allowed to warm to room temperature and the mixture is stirred overnight. The reaction vessel is cooled to $-78°$, the seal opened, and excess $H_2S$ allowed to evaporate. The residue is taken up in $CH_2Cl_2$ and filtered. The solvent is evaporated to give diethyl thioformamido-(p-nitrophenylsulfonyl)-methyl phosphonate.

Step E: 3-Acetoxy-2-Oxopropyl N-(diethylphosphono-p-nitrophenyloxysulfonylmethyl)-thioformimidate 8.2 g. diethyl thioformamido-(p-nitrophenylsulfonylmethylphosphonate is dissolved in 100 ml acetone. g. $K_2CO_3$ and 3.3 g. of 1-chloro-3-acetoxy-acetone is added and the mixture stirred overnight at room temperature. The precipitated salts are filtered off, the filtrate is evaporated, the residue is taken up in $CCl_4$, dried over $MgSO_4$ and filtered and evaporated to give 3-acetoxy-2-oxopropyl N-(diethylphosphono-p-nitrophenyloxysulfonylmethyl)-thioformimidate.

Step F: p-Nitrophenyl 5-acetoxymethyl-6H-1,3-thiazne-4-sulfonate

3-Acetoxy-2-oxopropyl N-(diethylphosphono-p-nitrophenoxy-sulfonylmethyl)-thioformimidate (4.08 g) is dissolved in 40 ml anhydrous dimethoxyethane under nitrogen and treated with 0.350 g of sodium hydride (57% in mineral oil). The reaction mixture is stirred at 50° for 3 hrs then cooled, diluted with chloroform and washed with pH 3 buffer and with brine, then dried and evaporated. The residue is chromatographed on silica gel to give p-nitrophenyl-5-acetoxymethyl-6H-1,3-thiazine-4-sulfonate.

Step G: p-Nitrophenophenyl d,1-3-acetoxymethyl-7$\alpha$-azido-3-cephem-4-sulfonate An ice-cold solution of 1.13 g of p-nitrophenyl 5-acetoxymethyl-6H-1,3-triazine-4-sulfonate and 0.5 g of triethylamine in methylene chloride (40 ml) is stirred under nitrogen while a solution of azidoacetyl chloride (0.590 g) in 20 ml methylene chloride is added dropwise over a period of 4 hours. The resulting solution is washed with water, dried over $MgSO_4$ and evaporated to give crude product. Chromatography on silica gel affords p-nitrophenyl d,1-3-acetoxymethyl-7$\alpha$-azido-3-cephem-4-sulfonate.

Step H: p-Nitrophenyl d,1-3-acetoxymethyl-7$\alpha$-amino 3-cephem-4-sulfonate 0.455 g of the p-nitrophenyl d, 1-3-acetoxymethyl-7$\alpha$-azido-3-cephem-4-sulfonate is dissolved in 20 ml $CH_2Cl_2$, cooled to 0° and 0.202 g of triethylamine is added and then $H_2S$ is bubbled in until the ri of an aliquot shows absence of azide.

The reaction mixture is evaporated, the residue is taken up in chloroform and washed once with a solution of $NaH_2PO_4$ and then with brine, then dried and evaporated to give p-nitrophenyl d,1,3-acetoxymethyl-7$\alpha$-amino-3-cephem-4-sulfonate.

Step I: p-nitrophenyl d, 1,3-acetoxymethyl-7$\alpha$-(p-nitrobenzylidene-amino)-3-cephem-4-sulfonate A mixture of p-nitrophenyl d,1,3-acetoxymethyl-7$\alpha$-amino-3-cephem-4-sulfonate (644mg), p-nitrobenzaldehyde (226 mg) anhydrous magnesium sulfate (4.0 g) and methylene chloride (30 ml) is stirred for two hours at room temperature. The mixture is filtered and the filtrate is evaporated under reduced pressure to yield p-nitrophenyl d,1,3-acetoxymethyl-7-α-(p-nitrobenzylideneamino)-3cephem-4-sulfonate.

Step J: p-Nitrophenyl d,1,3-acetoxymethyl-7β-(p-nitrobenzylideneamino-3-cephem-4-sulfonate A solution of p-nitrophenyl d,1,3-acetoxymethyl-7-α-(p-nitrobenzylideneamino)-3-cephem-4-sulfonate (845 mg) in 20 ml of anhydrous tetrahydrofuran is stirred at −78° under an atmosphere of nitrogen. Phenyllithium (0.65 ml of a 2.3 M solution in 7:3 benzene-ether) is added dropwise over a period of 15 minutes, and after an additional minute at −78°, a solution of water (270 mg) and acetic acid (255 mg) in tetrahydrofuran (25 ml) is added. The reaction mixture is allowed to warm to room temperature, then diluted with benzene (500 ml) and washed with six 250 ml portions of water. The second wash is acidified with pH 2 phosphate buffer and the fifth basified with pH 9 buffer. The benzene solution is dried over magnesium sulfate, filtered and evaporated in vacuo to give a mixture of p-nitrophenyl d, 1,3-acetoxymethyl-7-α-(p-nitrobenzylideneamino)-3-cephem-4-sulfonate and p-nitrophenyl d,1-3-acetoxymethyl-7-α-(p-nitrobenzylideneamino)-3-cephem-4-sulfonate.

Step K: p-Nitrophenyl d,1-3-acetoxymethyl-7-β-amino-3-cephem-4-sulfonate

The mixture of p-nitrophenyl d,1-3-acetoxymethyl-7-(p-nitrobenzylideneamino)-3-cephem-4-sulfonates obtained in the previous example is suspended in 40 ml of ether and p-toluene sulfonic acid hydrate (285 mg) is added. The mixture is stirred at room temperature for 3 hours, then filtered. The filter cake is washed with ether, then resuspended in 50 ml of chloroform and treated with N pH 9 phosphate buffer (50 ml). The chloroform solution is separated, dried over anhydrous magnesium sulfate and evaporated in vacuo to provide a mixture of p-nitrophenyl d,1-3-acetoxymethyl-7-β-amino-3-cephem-4-sulfonate and p-nitrophenyl d,1-3-acetoxymethyl-7-α-amino-3-cephem-4-sulfonate.

Step L: p-Nitrophenyl d,1-3-acetoxymethyl-7-β-(2-thienylacetamido)-3-cephem-4-sulfonate and p-nitrophenyl d,1-3-acetoxymethyl-7-α-(2-thienylacetamido)-3-cephem-4-sulfonate A mixture (515 mg) of p-nitrophenyl d,1-3-acetoxymethyl-7-β-amino-3-cephem-4-sulfonate and p-nitrophenyl d, 1-3-acetoxymethyl-7-α-amino-3-cephem-4-sulfonate is dissolved in anhydrous methylene chloride (8 ml.). The resulting solution is stirred at 0° under a nitrogen atmosphere. Pyridine (0.4 ml) is added followed by a solution of 2-thienylacetyl chloride (175 mg) in 3 ml of methylene chloride. The mixture is stirred at 0° for 15 minutes then diluted with 75 ml of benzene. The benzene solution is washed successively with pH 2 phosphate buffer, pH 9 phosphate buffer, water, and saturated brine, dried over magnesium sulfate and evaporated in vacuo to an oil. Chromatography of the crude product on 35 g of silica gel using ethyl acetate-benzene mixture as eluting solvent affords p-nitrophenyl d,1-3-acetoxymethyl-7β-(2-thienylacetamido)-3-cephem-4-sulfonate and p-nitrophenyl d,1-3-acetoxymethyl-7-α-(2-thienylacetamido)-3-cephem-4-sulfonate.

Step M: Sodium d,1,3-acetoxymethyl 7β-(2-thienylacetamido)-3-cephem-4-sulfonate A solution of p-nitrophenyl d,1-3-acetoxymethyl-7-β-(2-thienylacetamido)-3-cephem-4-sulfonate (225 mg) in 10 ml of dioxane and 2 ml of water is rapidly stirred and 0.1 N sodium hydroxide (5 ml) is added dropwise over a period of three hours. The mixture is stirred at room temperature for an additional 2 hours, then the dioxane is removed under reduced pressure. The residue is taken up in a mixture of water and ether and the aqueous layer is separated, extracted twice with ether, then freeze-dried giving the sodium salt of d,1-3-acetoxymethyl-7-β-(2-thienylacetamido)-3-cephem-4-sulfonate.

EXAMPLE 22 d,1-3-Acetoxymethyl-7β-(2-thienylacetamido)-3-cephem-4-sulfonamide.

To a solution of p-nitrophenyl d,1-3-acetoxymethyl-7-β-(2-thienylacetamido)-3-cephem-4-sulfonate (225 mg) in 10 ml of dioxane is added a solution of ammonia (17 mg) in dioxane (1 ml). The mixture is stirred at room temperature for 18 hours. The dioxane is removed under reduced pressure. The residue is taken up in chloroform and pH 2 phosphate buffer and the chloroform layer is separated and washed with pH 10 phosphate buffer. The chloroform layer is evaporated and the residue chromatographed on 20 g of silica gel. Elution with chloroform-ethyl acetate mixture yields d,l-3-acetoxymethyl-7-β-(2-thienylacetamido)-3-cephem-4-sulfonamide.

The following table lists examples of products of the invention which may be prepared in accordance with the methods illustrated in Flow Sheets I and II and described above in the specification and examples and which fall within the general formula:

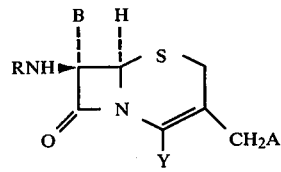

wherein R, B, A and Y are as indicated in Table I.

TABLE I

| Example No. | R | B | A | Y |
|---|---|---|---|---|
| 23 | ⌬-CHC(=O)- with NH$_2$ | —OCH$_3$ | —OC(=O)—NH$_2$ | SO$_3$Na |
| 24 | thienyl-CH$_2$C(=O)- | —OCH$_3$ | —OCCH$_3$ (O) | PO(OH)(ONa) |

TABLE I-continued

| Example No. | R | B | A | Y |
|---|---|---|---|---|
| 25 | furan-CH$_2$C(O)- | —OCH$_3$ | —OC(O)NH$_2$ | PO(ONa)$_2$ |
| 26 | HO-C$_6$H$_4$-CH(NH$_2$)-C(O)- | —OCH$_3$ | —OC(O)NH$_2$ | PO(ONa)$_2$ |
| 27 | thiazole-C(=)-CH$_2$C(O)- | H | —OCH$_3$ | SO$_3$Na |
| 28 | phenyl-CH(tetrazole-NH)-C(O)- | H | —O-C(O)CH$_3$ | SO$_2$NH$_2$ |
| 29 | thiophene-CH$_2$C(O)- | OCH$_3$ | —OC(O)CH$_3$ | SO$_3$Na |
| 30 | phenyl-CH(COOH)-C(O)- | OCH$_3$ | —OC(O)NH$_2$ | PO(ONa)$_2$ |
| 31 | thiophene-CH(COOH)-C(O)- | OCH$_3$ | —OC(O)NH$_2$ | PO(ONa)$_2$ |
| 32 | phenyl-CH$_2$C(O)- | OCH$_3$ | —OC(O)NH$_2$ | SO$_2$NH$_2$ |
| 33 | Br-C$_6$H$_4$-CH$_2$C(O)- | H | H | PO(ONa)$_2$ |
| 34 | NH$_2$CH$_2$-C$_6$H$_4$-CH$_2$C(O)- | H | H | SO$_2$NH$_2$ |
| 35 | HOC(O)-CH$_2$-C$_6$H$_4$-CH$_2$C(O)- | H | —OC(O)NH$_2$ | PO(ONa)$_2$ |
| 36 | HOC(O)-NH-CH$_2$-C$_6$H$_4$-CH$_2$C(O)- | H | —OC(O)NHCH$_2$CCl$_3$ | PO(OCH$_3$)$_2$ |
| 37 | NO$_2$-furan-CH$_2$C(O)- | H | —Oφ | SO$_3$Na |
| 38 | furan-CH$_2$C(O)- | —OCH$_3$ | CH$_3$O-C$_6$H$_4$-OCH$_2$- | PO(ONa)$_2$ |
| 39 | Cl-thiophene-CH$_2$C(O)- | H | Cl | PO(OCH$_3$)$_2$ |

TABLE I-continued

| Example No. | R | B | A | Y |
|---|---|---|---|---|
| 40 | CH₃O-[thiophene]-CH₂C(O)- | H | Br | PO(ONa)₂ |
| 41 | [thiophene with NH-C(=NH)NH₂ substituent]-CHC(O)- | H | H | SO₂NH₂ |
| 42 | CH₃-[thiophene]-CH₂C(O)- | H | -OCH₂-C₆H₄-NO₂ | SO₃Na |
| 43 | -C(O)CH₂-[thiazole]- | H | -OC(O)CH₃ | PO(ONa)₂ |
| 44 | CH₃O-[thiazole]-CH₂C(O)- | -OCH₃ | -OCH₃ | SO₂NH₂ |
| 45 | [thiazole]-CH₂C(O)- | H | -OC(O)NH₂ | PO(OCH₃)₂ |
| 46 | CH₃-[thiazole]-CH₂C(O)- | H | -OC(O)NHCH₂CCl₃ | SO₃Na |
| 47 | Cl-[thiazole]-CH₂C(O)- | H | -OC(O)CH₃ | PO(OH)(ONa) |
| 48 | CH₃-[thiadiazole]-CH₂C(O)- | -OCH₃ | -OCH₂OCH₃ | PO(OH)₂ |
| 49 | [thiadiazole]-CH₂C(O)- | -OCH₃ | Cl | PO(ONa)₂ |
| 50 | CH₃-[thiadiazole]-CH₂C(O)- | H | -OC(O)CH(CH₃)₂ | SO₂NH₂ |
| 51 | Cl-[thiadiazole]-CH₂C(O)- | H | -OC(O)CH(CH₃)₂ | SO₂NH₂ |
| 52 | CH₃O-[thiadiazole]-CH₂C(O)- | H | -OC(O)NH₂ | PO(OH)₂ |
| 53 | C₆H₅-SCH₂C(O)- | -OCH₃ | -OC(O)NH₂ | PO(ONa)₂ |
| 54 | [pyridine]-SCH₂C(O)- | H | -OC(O)NH₂ | SO₂NH₂ |
| 55 | CNCH₂C(O)- | H | -OC(O)CH₃ | SO₃Na |

TABLE I-continued

| Example No. | R | B | A | Y |
|---|---|---|---|---|
| 56 | triazolyl-N-CH$_2$C(=O)- (N=N-C=N with CH$_2$C(O)-) | H | H | SO$_3$Na |
| 57 | phenyl-CHF-C(=O)- | H | -Oφ | PO(ONa)$_2$ |
| 58 | 2-thienyl-CH(NH$_2$)-C(=O)- | -OCH$_3$ | -Oφ | PO(ONa)$_2$ |
| 59 | 2-thienyl-CH(NH$_2$)-C(=O)- | H | -Oφ | PO(OH)$_2$ |
| 60 | 2-thienyl-C(=O)CH$_2$C(=O)- | H | -OC(=O)NH$_2$ | SO$_3$Na |
| 61 | phenyl-CH(PO(OH)$_2$)-C(=O)- | H | H | SO$_2$NH$_2$ |
| 62 | phenyl-CH(NHSO$_3$H)-C(=O)- | H | OCH$_3$ | PO(ONa)$_2$ |
| 63 | phenyl-CH(OH)-C(=O)- | -OCH$_3$ | -OC(=O)NH$_2$ | SO$_3$Na |
| 64 | phenyl-CH(SO$_2$(OH))-C(=O)- | -OCH$_3$ | -OC(=O)NH$_2$ | PO(ONa)$_2$ |
| 65 | 2-thienyl-CH$_2$C(=O)- | H | -OC(=O)NH$_2$ | PO(OH)(ONa) |

It will be appreciated by one skilled in the art that the products illustrated in the chart above, wherein B = H or methoxy, are merely representative of the variety and scope of compounds enbraced by this invention. Corresponding novel useful antibiotic compounds wherein B = CH$_3$ or SR″ shall also be obtained in accordance with the teachings of the invention. The general description of the inventive processes of preparing 7-methyl derivatives is described in the following Example 66. The preparation of other thio lower alkyl derivatives can be readily accomplished using the methods described in Example 7, Step A, using other loweralkylsulfinyl chlorides as reactants.

EXAMPLE 66

Sodium-3-acetoxymethyl-7β-(2-thienyl)acetamido-7-methyl-3-cephem-4-sulfonate

The compound p-nitrophenyl-3-acetoxymethyl-7-(p-nitrobenzylideneamino)-3-cephem-4-sulfonate obtained as in Example 21, Step J, 306 mg., is dissolved in 10 ml of anhydrous tetrahydrofuran at −78° C. Phenyl lithium (0.22 ml of 2.3 M solution in tetrahydrofuran) is added slowly under a nitrogen atmosphere. Methyliodide (0.4 ml) in 10 ml of N,N-dimethylformamide is then added dropwise. The reaction mixture is warmed to room temperature, poured into ice water and extracted with 3 ×20 ml ethyl acetate. The mixed organic layers are washed with 2 ×10 ml brine and dried over magnesium sulfate. The product, p-nitrophenyl-3-acetoxymethyl-7α-methyl-7-p-nitrobenzylideneamino-3-cephem-4-sulfonate is recovered.

This latter product is then reacted with p-toluene sulfonic acid as in Example 21, Step K, thereby yielding p-nitrophenyl 3-acetoxymethyl-7β-amino-7-α-methyl-3-cephem-4-sulfonate.

This latter can be acylated by reaction with 2-thienylacetyl chloride to yield the product, p-nitrophenyl-3-acetoxymethyl-7β-(2-thienyl)acetamido-7-methyl-3-cephem-4-sulfonate, then deblocked to yield one sodium salt, as described in Example 21, Steps L and M.

The products of this invention (I) forms a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-lower-alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts can be mono-salts such as the monosodium salt obtained by treating one equivalent of sodium hydroxide with one equivalent of the product (I), also mixed di-salts may be obtained by treating one equivalent of a mono-salt with one equivalent of a different base. Alternatively, salts may be obtained by treating one equivalent of a base having a divalent cation, such as calcium hydroxide, with one equivalent of the product (I). In addition, mixed salts and esters such as those obtained by treating the product (I) with one equivalent of sodium hydroxide and then with one equivalent of lactic acid are also within the scope of this invention.

The salts of this invention are pharmacologically acceptable nontoxic derivatives which can be used as the active ingredient in suitable unit-dosage pharmaceutical forms. Also, they may be combined with other drugs to provide compositions having a broad spectrum of activity. In addition, the instant salts and, also, the corresponding ester and amide derivatives, have utility as intermediates in preparing the carboxylic acid product illustrated by formula I, supra.

The products (I) may also be converted to their corresponding mono- and di- esters and mono- and di-amides for example, the pivaloyloxymethyl or dibenzhydryl esters or alkyl, cycloalkyl, aryl or aralkyl esters, for example, the methyl, ethyl, cyclohexyl, phenyl and benzyl esters or amides, diamides, N-lower alkyl amides, N,N-di-lower alkylamides, N-aralkylamides, N-diaralkylamides or heterocyclic amides such as the N-methyl and N-ethylamide, N,N-dimethylamide, N,N-diethylamide, N-benzylamide, N,N-dibenzylamide, piperidide, pyrrolidide, morpholide and the like.

Of particular interest are the following esters:
2-thienyl,
methylthiobutyl,
methylallyl,
3-penten-1-yl,
4-penten-1-yl,
3-pentyn-1-yl,
methylthioethyl,
benzyl,
3-buten-1-yl and
2-buten-1-yl.

Methods for the preparation of the esters and amide derivatives include the reaction of the acid product (I) or corresponding acid halide with an alcohol or phenol, for example, methanol, ethanol, cyclohexanol, phenol, benzyl alcohol, dibenzhydrol and the like. The amide derivatives may be obtained by treating the corresponding acid halide with ammonia or with an appropriate alkylamine, dialkylamine, aralkylamine or heterocyclic amine. These and other conventional methods for the preparation of the esters and amides will be obvious to those skilled in the art.

Thus the novel cephalosporins are valuable antimicrobial substances which are active against various gram-positive and gram-negative pathogens such as *Bacillus subtilis, Salmonella schottmuelleri* and *Proteus vulgaris*. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups elixirs and the like which can be prepared in accordance with procedures well known in this art.

Pharmaceutically acceptable salts which may be formed using procedures well known to the art from the compounds of the invention include (a) inorganic base salts such as alkali metal, e.g. sodium and potassium, alkaline earth e.g. calcium, and organic base salts, e.g. procaine and dibenzylethylene diamine salts and (b) acid addition salts e.g. with hydrochloric, hydrobromic, sulphuric, nitric, phosphoric, toluene-p-sulphonic and methanesulphonic acids. In addition to salts, the novel cephalosporins of the invention may be administered in the form of esters, including those discussed above. Examples of esters that might be mentioned are esters of alcohols, phenols, mercaptans, and thiophenols of the general formula $PO(OR_4)$ or $SO_2OR_4$ wherein $R_4$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(p-methylphenyl)ethyl, 2-(p-methylphenyl)sulfonylethyl, 2-methylaminoethyl, 2-chloro-(or bromo) ethyl, benzyl, a substituted benzyl group such as p-nitrobenzyl, p-methoxybenzyl, 3,5-dinitrobenzyl, 2-4,6-trimethylbenzyl, 3,5-dichloro-4-hydroxybenzyl, and the like, a benzhydryl or substituted benzhydryl group such as p-methoxybenzhydryl, an acyloxy alkyl group such as acetoxymethyl, pivaloyloxymethyl, an alkoxy group such as methoxymethyl, or a monocyclic aryl group for example phenyl or substituted phenyl such as p-nitrophenyl or 3,5-dinitrophenyl of interest are the alkenyl esters (e.g. 3-buten-1-yl). These esters are readily prepared in accordance with processes well known in this art.

The novel cephalosporins are valuable antibiotics active against various gram-positive and gram negative bacteria and, accordingly, find utility in human and veterinary medicine. The compounds of this invention can therefore be used as antibacterial drugs for treating infections caused by gram-positive or gram-negative bacteria, for example against *Staphylococcus aureus* (penicilline resistant), *Escherichia coli, Klebsiella pneumoniae, Salmonella Typhosa, Pseudomonas* and Bacterium proteus. The antibacterial cephalosporins of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The examples which preceded illustrate the methods by which the products of this invention may be obtained. However, the examples are illustrative only and it should be apparent to one having ordinary skill in the art that this invention includes the functionally equivalent products and methods for their preparation. Therefore, any modification of the synthesis described herein which results in the formation of an identical product should be construed as constituting an analogous method. The claimed process is capable of wide variation and modification and any minor departure or extension is considered as being within the skill of the artisan and as falling within the scope of this invention.

What is claimed is:

1. A compound of the formula

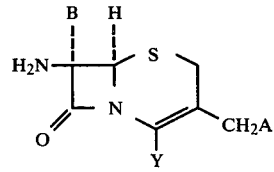

wherein B is hydrogen, or methoxy;
A is selected from the group consisting of hydrogen, acetoxy, amino, acetamido, carbamoylamino, N,N-dimethylamino, N-(2-chloroethyl)amino, 5-cyanotriazol-1-yl, 4-methoxycarbonyltriazol-1-yl, pyridinium, 3-methylpyridinium, 4-methylpyridinium, 3-chloropyridinium, 3-bromopyridinium, 3-iodopyridinium, 4-carbamoylpyridinium,; 4-(N-carbomethoxycarboxymethyl)pyridinium, 4-(hydroxymethyl)pyridinium, 4-trifluoromethyl)-pyridinium, quinolinium, picolinium and lutidinium; and Y is a radical of the formula $PO(OH)_2$, $PO(OH)(OR'')$ wherein R'' is loweralkyl of 1-6 carbon atoms; $SO_2(OH)$; or $SO_2NH_2$; and the non-toxic, pharmaceutically acceptable salts and esters thereof.

* * * * *